US011497795B2

(12) United States Patent
Sakai et al.

(10) Patent No.: US 11,497,795 B2
(45) Date of Patent: Nov. 15, 2022

(54) MEDICAMENT FOR MITIGATING CONDITIONS AND/OR SUPPRESSING ONSET OF PERIPHERAL NEUROPATHY INDUCED BY ANTI-MALIGNANT TUMOR AGENT

(71) Applicant: Asahi Kasei Pharma Corporation, Tokyo (JP)

(72) Inventors: Takumi Sakai, Tokyo (JP); Genichi Kusakawa, Tokyo (JP); Yugo Uchida, Tokyo (JP)

(73) Assignee: ASAHI KASEI PHARMA CORPORATION, Tokyo (JP)

( * ) Notice: Subject to any disclaimer, the term of this patent is extended or adjusted under 35 U.S.C. 154(b) by 0 days.

(21) Appl. No.: 16/657,507

(22) Filed: Oct. 18, 2019

(65) Prior Publication Data

US 2020/0101139 A1  Apr. 2, 2020

Related U.S. Application Data

(63) Continuation of application No. PCT/JP2019/038066, filed on Sep. 27, 2019.

(30) Foreign Application Priority Data

Sep. 28, 2018  (JP) .............................. JP2018-183447

(51) Int. Cl.
*A61K 38/36* (2006.01)
*A61P 25/02* (2006.01)

(52) U.S. Cl.
CPC ............ *A61K 38/366* (2013.01); *A61P 25/02* (2018.01)

(58) Field of Classification Search
CPC .............................. A61K 38/366; A61P 25/02
See application file for complete search history.

(56) References Cited

U.S. PATENT DOCUMENTS

| 5,043,425 A | 8/1991 | Aoki et al. |
| 5,516,695 A | 5/1996 | Kim et al. |
| 5,695,964 A | 12/1997 | Nii et al. |
| 5,801,160 A | 9/1998 | Sandage et al. |
| 5,827,832 A | 10/1998 | Sandage, Jr. et al. |
| 5,872,108 A | 2/1999 | Sandage, Jr. et al. |
| 5,916,874 A | 6/1999 | Fujiwara et al. |
| 5,976,523 A | 11/1999 | Awaya et al. |
| 6,034,060 A | 3/2000 | Yamamoto et al. |
| 8,440,832 B2 | 5/2013 | Attala et al. |
| 2002/0111296 A1 | 8/2002 | Festoff et al. |
| 2004/0002446 A1 | 1/2004 | Festoff et al. |
| 2008/0280774 A1 | 11/2008 | Burczynski et al. |
| 2009/0143281 A1 | 6/2009 | Festoff et al. |
| 2010/0204220 A1 | 8/2010 | Attala et al. |
| 2011/0052723 A1 | 3/2011 | Baeyens-Cabrera et al. |
| 2011/0207803 A1 | 8/2011 | Nabeta |
| 2011/0212900 A1 | 9/2011 | Ikezoe et al. |
| 2011/0281876 A1 | 11/2011 | Sun |
| 2011/0287110 A1 | 11/2011 | Dewhirst et al. |
| 2012/0039866 A1 | 2/2012 | Salvemini |
| 2013/0237482 A1 | 9/2013 | Tsuruta et al. |
| 2013/0237536 A1 | 9/2013 | Attala et al. |
| 2015/0148296 A1* | 5/2015 | Kawabata ............ A61K 38/366 514/13.5 |

FOREIGN PATENT DOCUMENTS

| EP | 0312598 A1 | 4/1989 |
| EP | 0356836 A2 | 3/1990 |
| EP | 0489180 A1 | 6/1992 |
| EP | 0743066 A2 | 11/1996 |
| EP | 0763360 A1 | 3/1997 |
| JP | 64-6219 A | 1/1989 |
| JP | 3-86900 A | 4/1991 |
| JP | 8-3065 A | 1/1996 |
| JP | 8-283174 A | 10/1996 |
| JP | 8-301783 A | 11/1996 |
| JP | 9-20677 A | 1/1997 |
| JP | 10-1439 A | 1/1998 |

(Continued)

OTHER PUBLICATIONS

NCI Drug Dictionary page for thrombomodulin alfa, 1 page (Year: 2020).*
Watanabe et al., Frontiers in Medicine, Feb. 2017 vol. 4, article 15, 8 pages (Year: 2017).*
Nishida et al., Toxicology. Jul. 15, 2016;365:48-58 (Abstract only provided) (Year: 2016).*
Uchida et al., Supportive Care in Cancer, (Jun. 2019) vol. 27, No. 1, Supp. Supplement, pp. S13-S14. Abstract No. PS23 (Year: 2019).*
Kato et al., Annals of Oncology, (Oct. 2018) vol. 29, Supp. Supplement 8, pp. viii199. Abstract No. 599P (Year: 2018).*
Recomodulin 12800 Product Sheet, reexamined Dec. 2017, 19 pages (Year: 2017).*

(Continued)

*Primary Examiner* — Larry D Riggs, II
*Assistant Examiner* — Joseph Fischer
(74) *Attorney, Agent, or Firm* — Birch, Stewart, Kolasch & Birch, LLP

(57) ABSTRACT

An object of the present invention is to provide an effective and safe medicament having effects for mitigating conditions and/or suppressing onset of a peripheral neuropathy induced by administration of an anti-malignant tumor agent, oxaliplatin, in a human cancer patient receiving an anti-malignant tumor treatment with oxaliplatin. There is provided a medicament for mitigating conditions and/or suppressing onset of a peripheral neuropathy induced by oxaliplatin in an anti-malignant tumor treatment consisting of repetition of a single cycle comprising intravenous administration of oxaliplatin to a human cancer patient and following drug withdrawal, which contains thrombomodulin for intravenously administering 0.06 mg/kg of thrombomodulin once per said single cycle of the treatment on the first day of each said cycle as an active ingredient.

19 Claims, 1 Drawing Sheet

Specification includes a Sequence Listing.

(56) References Cited

FOREIGN PATENT DOCUMENTS

| | | |
|---|---|---|
| JP | 2011-178687 A | 9/2011 |
| JP | 2012-1543 A | 1/2012 |
| JP | 6124417 B2 | 5/2017 |
| JP | 2018-95652 A | 6/2018 |
| WO | WO 92/00325 A1 | 1/1992 |
| WO | WO 96/22108 A1 | 7/1996 |
| WO | WO 96/27380 A1 | 9/1996 |
| WO | WO 03/061687 A1 | 7/2003 |
| WO | WO 2009/103487 A1 | 8/2009 |
| WO | WO 2010/006634 A1 | 1/2010 |
| WO | WO 2013/073545 A1 | 5/2013 |

OTHER PUBLICATIONS

CCO Formulary for mFOLFOX6, Oct. 2016, 9 pages (Year: 2016).*

Jeon et al., Adjuvant Chemotherapy Using the FOLFOX Regimen in Colon Cancer, J Korean Soc Coloproctol 2011;27(3):140-146 (Year: 2011).*

Jeon et al., J Korean Soc Coloproctol 2011;27(3):140-146 (Year: 2011).*

Abeyama et al., "The N-Terminal domain of thrombomodulin sequesters high-mobility group-B1 protein, a novel antiinflammatory mechanism", The Journal of Clinical Investigation, vol. 115, No. 5, May 2005, pp. 1267-1274.

Dougherty et al., "Taxol-induced sensory disturbance is characterized by preferential impairment of myelinated fiber function in cancer patients", Pain, vol. 109, 2004, pp. 132-142.

Egashira et al., "The Current State of the Drugs for Treatmen of Peripheral Neuropathy Induced by Anticancer Drugs", Folia Pharmacol. Jpn., vol. 136, 2010, pp. 275-279 (16 pages total), with an English translation.

Flatters et al., "Acetyl-L-carnitine prevents and reduces paclitaxel-induced painful peripheral neuropathy", Neuroscience Letters, vol. 397, 2006, pp. 219-223.

Ghelardini et al., "Effects of a New Potent Analog of Tocainide on hNav1.7 Sodium Channels and In Vivo Neuropathic Pain Models", Neuroscience, vol. 169, 2010, pp. 863-873.

Ikezoe et al., "Successful treatment of sinusoidal obstructive syndrome after hematopoietic stem cell transplantation with recombinant human soluble thrombomodulin", Bone Marrow Transplantation, vol. 45, 2010 (published online Aug. 31, 2009), pp. 783-785.

Ito et al., "Proteolytic Cleavage of High Mobility Group Box 1 Protein by Thrombin-Thrombomodulin Complexes", Arteriosclerosis, Thrombosis, and Vascular Biology, vol. 28, Oct. 2008 (published online Jul. 3, 2008), pp. 1825-1830 (18 pages total), with supplemental information.

Jolivalt et al., "Therapeutic efficacy of prosaposin-derived peptide on different models of allodynia", Pain, vol. 121, 2006, pp. 14-21.

Otoshi et al., "Anti-HMGB1 Neutralization Antibody Improves Pain-Related Behavior Induced by Application of Autologous Nucleus Pulposus Onto Nerve Roots in Rats", Spine, vol. 36, No. 11, May 2011, pp. E692-E698.

Shibasaki et al., "Induction of high mobility group box-1 in dorsal root ganglion contributes to pain hypersensitivity after peripheral nerve injury", Pain, vol. 149, 2010, pp. 514-521.

Shibasaki, "KAKEN—Advances in the Understanding of Mechanisms of Intracellular Signaling by Thrombomodulin in the Hypersensitivity State", FY2010 Annual Report, Dec. 10, 2014, 6 pages total, with English translation.

Smith et al., "Treating Pain from Chemotherapy-induced Peripheral Neuropathy", NCI Cancer Bulletin, vol. 7, No. 4, Feb. 23, 2010, pp. 1-2.

Suzuki el al., "Structure and expression of human thrombomodulin, a thrombin receptor on endothelium acting as a cofactor for protein C activation", The EMBO Journal, vol. 6, No. 7, 1987, pp. 1891-1897.

The 121st Kinki Branch Meeting in Tokushima "Program and Abstracts for the 121st Kinki Branch Meeting of the Japanese Pharmacological Society", The Japanese Pharmacological Society, Jun. 29, 2012, 12 pages total, with English translation.

Author Unknown, "Interview Form,", Dec. 2014, pp. 1-29 (39 pages total), with a partial English translation.

Author Unknown, "Recomodulin® Intravenous Infusion 12800 Package Insert," Standard Commodity of Japan Classification No. 873339, Ver. 10, Aug. 2018, pp. 1-16 (19 pages total), with English translation.

Damaske et al., "Leucovorin-induced hypersensitivity reaction", Journal of Oncology Pharmacy Practice, vol. 18, No. 1, 2011, pp. 136-139 (5 pages total).

Delanian et al., "Radiation-induced neuropathy in cancer survivors", Radiotherapy and Oncology, vol. 105, 2012, pp. 273-282.

Fallon, "Neuropathic pain in cancer", British Journal of Anaesthesia, vol. 111, No. 1, 2013, pp. 105-111.

Fujii et al., "Calcineurin Inhibitor-Induced Irreversible Neuropathic Pain after Allogeneic Hematopoietic Stem Cell Transplantation," International Journal of Hematology, 2006, vol. 83, pp. 459-461.

Hafer-Macko et al., "Thrombomodulin Deficiency in Human Diabetic Nerve Microvasculature," Diabetes, vol. 51, Jun. 2002, pp. 1957-1963.

Hershman et al., "Prevention and Management of Chemotherapy-Induced Peripheral Neuropathy in Survivors of Adult Cancers: American Society of Clinical Oncology Clinical Practice Guideline Summary", Journal of Oncology Practice, vol. 10, No. 6, Nov. 2014, pp. e421-e424.

Moll et al., "Phase I Study of a Novel Recombinant Human Soluble Thrombomodulin, ART-123", Journal of Thrombosis and Haemostasis, vol. 2, 2004, pp. 1745-1751.

Nurmikko et al., "Sativex successfully treats neuropathic pain characterised by allodynia: A randomised, double-blind, placebo-controlled clinical trial," Pain, vol. 133, 2007, pp. 210-220.

Saif et al., "Management of Oxaliplatin-induced peripheral neuropathy", Therapeutics and Clinical Risk Management, vol. 1, No. 4, 2005, pp. 249-258.

Tanaka et al., "Chemotherapy," New Pharmacology, Chapter XII, 2002, pp. 568-581 (38 pages total), with an English translation.

Wen et al., "Human Thrombomodulin: Complete cDNA Sequence and Chromosome Localization of the Gene", Biochemistry, vol. 26, No. 14, 1987, pp. 4350-4357.

Wolf et al., "Chemotherapy-induced peripheral neuropathy: Prevention and treatment strategies", European Journal of Cancer, vol. 44, 2008, pp. 1507-1515.

Zhu et al., "Repeated administration of mirtazapine inhibits development of hyperalgesia/allodynia and activation of NF-κB in a rat model of neuropathic pain," Neuroscience Letters, vol. 433, 2008, pp. 33-37.

Hayashi et al., "Influence of anticoagulant on preventive effect of thrombomodulin alpha for oxaliplatin-induced peripheral nerve disorder," Fukuoka (Poster), 2018, 3 pages total, with an English translation.

Hayashi et al., "Molecular mechanisms for the recombinant soluble thrombomodulin-induced suppression of HMGB1-dependent allodynia in mice: Roles of the N-terminal domains of thrombomodulin," 18th World Congress of Basic and Clinical Pharmacology, Jul. 4, 2018, 2 pages total.

Hayashi et al., "The suppressive effect of thrombomodulin alpha on the HMGB1-induced hyperalgesia is dependent on thrombin," 15 pages total.

Hayashi et al., "Thrombin-dependent inhibition of HMGB1-induced mechanical allodynia by thrombomodulin in mice," Neuroscience 2017, Nov. 12, 2017, 3 pages total.

Hayashi et al., "Thrombomodulin alpha thrombin dependently decomposes HMGB1 to suppress inflammatory pain," Kyoto (Poster), 2017, 4 pages total, with an English translation.

Hayashi et al.,"Analysis of molecular mechanism and thrombin dependency of action of thrombomodulin alpha for suppressing HMGB1-induced hyperalgesia," Kyoto (Oral), 2016, 17 pages total, with an English translation.

International Search Report for International Application No. PCT/JP2019/038066, dated Nov. 5, 2019, with an English translation.

Kamitani et al., "Role of intranuclear protein HMGB1 in expression and maintenance of vincristine-induced neuropathic pain," 65th (poster), 2015, 4 pages total, with an English translation.

(56) References Cited

OTHER PUBLICATIONS

Kawabata et al., "Middle Molecular Weight Heparinylphenylalanine Prevents the Development of Chemotherapy-Induced Peripheral Neuropathy in Mice," 17th World Congress on Pain, 2018, 1 page total.

Kawabata et al., "Prevention and reversal of chemotherapy-induced neuropathic pain by HMGB1 neutralization in rodents," 9th FENS Forum of European Neuroscience, Milan, Italy, Jul. 5-9, 2014, 2 pages total.

Kawabata et al., "Preventive and therapeutic effects of recombinant human soluble thrombomodulin on inflammatory pain and cancer chemotherapy induced neuropathic pain . . . " Saitama (Oral), Jul. 12-13, 2013, 3 pages total, with an English translation.

Kawabata et al., "Roles of DAMPs in the regulation of neuropathology," Symposium 31, 2018, 2 pages total.

Kawaishi et al, "Inactivation of HMGB1 with its neutralizaing antibody and recombinant human soluble thrombomodulin suppresses paclitaxel-induced neuropathy in rats and mice," The 87th Annual Meeting of the Japanese Pharmacological Society, Sendai, Japan, Mar. 19-21, 2014, 2 pages total.

Minami et al., "Thrombomodulin alfa prevents oxaliplatin-induced neuropathic symptoms through activation of thrombin-activatable fibrinolysis inhibitor and protein C without affecting anti-tumor activity," European Journal of Pharmacology, May 11, 2020, 38 pages total.

Nakatake et al., "Effect of extracellular HMGB1 on neuritogenesis in mouse dorsal root ganglion neurons and its inhibition by thrombomodulin alfa," 11th FENS Forum of Neuroscience, 2018, 2 pages total.

Nakatake et al., "HMGB1-induced neurite outgrowth in mouse dorsal root ganglion neurons and its inhibition by thrombomodulin," Neuroscience 2017, Nov. 11, 2017, 3 pages total.

Nishida et al., "Involvement of high mobility group box 1 in the development and maintenance of chemotherapy-induced peripheral neuropathy in rats," Toxicology, 2016, vol. 365, pp. 48-58, 11 pages total.

Nishida et al., "Preventive or therapeutic effects of anti-HMGB1 neutralizing antibody and recombinant human soluble thrombomodulin in rats with neuropathy induced by vincristine," The 87th Annual Meeting of the Japanese Pharmacological Society, Sendai, Japan, Mar. 19-21, 2014, 2 pages total.

Sekiguchi et al., "Paclitaxel-induced HMGB1 release from macrophages and its implication for peripheral neuropathy in mice: Evidence for a neuroimmune crosstalk," Neuropharmacology, 2018, vol. 141, pp. 201-213, 13 pages total.

Tanaka et al., "Recombinant human soluble thrombomodulin prevents peripheral HMGB1-dependent hyperalgesia in rats," British Journal of Pharmacology, 2013, vol. 170, pp. 1233-1241, 9 pages total.

Tsubota et al, "Treatment of pain using human soluble thrombomodulin: involvement of HMGB1 adsorption/decomposition prompting action," 2014, pp. 28-29, 4 pages total, with an English abstract.

Tsubota et al., "Involvement of HMGB1 in oxaliplatin-induced neuropathic pain: about origin and target molecule thereof," Sendai, 2016, 4 pages total, with an English abstract.

Tsubota et al., "Recombinant human soluble thrombomodulin exhibits preventive and therapeutic effects in paclitaxel-induced neuropathic pain model by suppressing HMGB1 signal," Nagoya (Oral), Jul. 12, 2013, 4 pages total, with an English abstract.

Tsubota et al., "Role of non-macrophage cell-derived HMGB1 in oxaliplatin-induced peripheral neuropathy and its prevention by the thrombin/thrombomodulin system in rodents: negative impact of anticoagulants," Journal of Neuroinflammation, 2019, vol. 16, No. 199, pp. 1-16.

Tsubota et al., Biological Function and Drug Discovery Symposium, Aug. 25-26, 2016, 12 pages total.

Tsujita et al., "Thrombomodulin alpha suppresses HMGB1-induced hyperalgesia in a thrombin dependent manner," Abstracts of the 39th Annual Meeting of JASP, Kobe (Poster), 2017, 4 pages total, with an English abstract.

Kato et al., "Efficacy and safety of a recombinant soluble human thrombomodulin (ART-123) in preventing oxaliplatin induced peripheral neuropathy (OIPN): Results of a placebo-controlled, randomized, double-blind phase II study," Annals of Oncology, vol. 29, Oct. 2018, 1 page.

Office Action for Taiwanese Patent Application No. 108135247 dated Mar. 15, 2021, including an English translation of Office Action.

Weickhardt et al., "Oxaliplatin-Induced Neuropathy in Colorectal Cancer," Journal of Oncology, vol. 2011, 2011, 7 pages.

Russian Office Action and Search Report for corresponding Russian Application No. 2021107897, dated Oct. 27, 2021, with English translation.

Canadian Office Action for Canadian Application No. 3,112,679, dated Feb. 28, 2022.

International Preliminary Report on Patentability and Written Opinion of the International Searching Authority (Forms PCT/IB/338, PCT/IB/373, and PCT/ISA/237) for International Application No. PCT/JP2019/038066, dated Apr. 8, 2021, with an English translation.

Japanese Notice of Reasons for Refusal for Japanese Application No. 2020-549413, dated Mar. 1, 2022, with an English translation.

Russian Office Action issued in Patent Application No. 2021107897 dated Apr. 28, 2022.

Extended European Search Report for European Application No. 19865629.0, dated Jun. 22, 2022.

Gebremedhn et al., "The incidence of acute oxaliplatin-induced neuropathy and its impact on treatment in the first cycle: a systematic review," BMC Cancer, vol. 18, No. 410, 2018, pp. 1-10.

Office Action Issued in Japanese Patent Application No. 2020-549413 dated Sep. 20, 2022.

* cited by examiner

[Fig. 1]
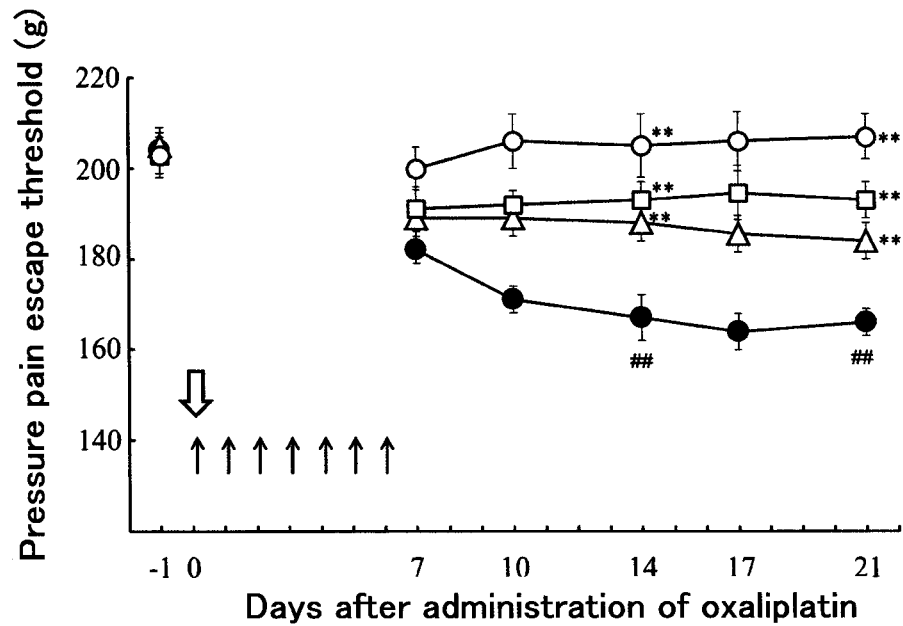
[Fig. 2]
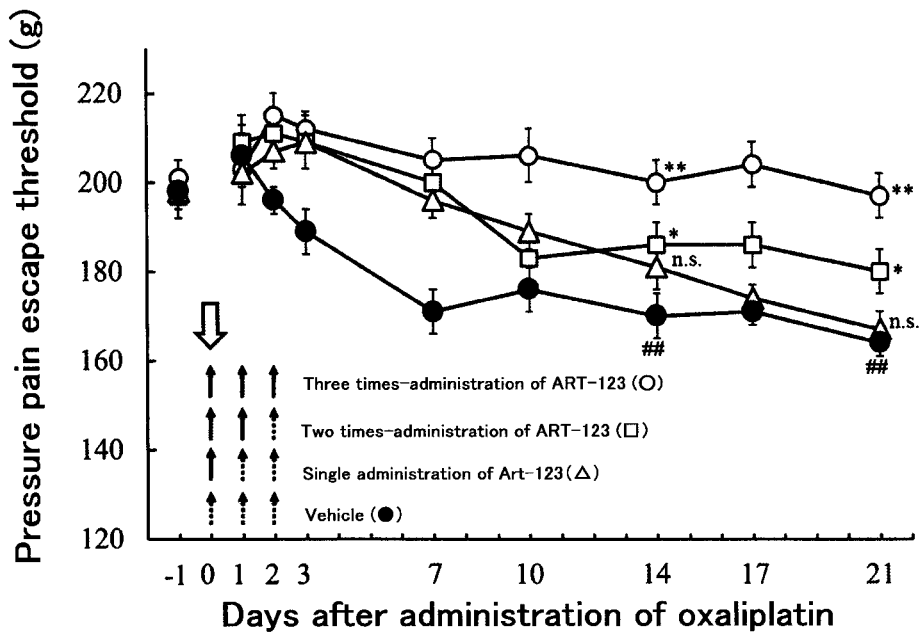

SEQUENCE LISTING

```
<160> NUMBER OF SEQ ID NOS: 5

<210> SEQ ID NO 1
<211> LENGTH: 516
<212> TYPE: PRT
<213> ORGANISM: human

<400> SEQUENCE: 1

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
                180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
                260                 265                 270

Leu Gln Ala Asp Gly Arg Ser Cys Thr Ala Ser Ala Thr Gln Ser Cys
            275                 280                 285

Asn Asp Leu Cys Glu His Phe Cys Val Pro Asn Pro Asp Gln Pro Gly
        290                 295                 300
```

```
Ser Tyr Ser Cys Met Cys Glu Thr Gly Tyr Arg Leu Ala Ala Asp Gln
305                 310                 315                 320

His Arg Cys Glu Asp Val Asp Cys Ile Leu Glu Pro Ser Pro Cys
            325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
    450                 455                 460

Ile Cys Gly Pro Asp Ser Ala Leu Val Arg His Ile Gly Thr Asp Cys
465                 470                 475                 480

Asp Ser Gly Lys Val Asp Gly Gly Asp Ser Gly Ser Gly Glu Pro Pro
            485                 490                 495

Pro Ser Pro Thr Pro Gly Ser Thr Leu Thr Pro Ala Val Gly Leu
            500                 505                 510

Val His Ser Gly
        515

<210> SEQ ID NO 2
<211> LENGTH: 1548
<212> TYPE: DNA
<213> ORGANISM: human

<400> SEQUENCE: 2
atgcttgggg tcctggtcct tggcgcgctg gccctggccg gcctgggggtt ccccgcaccc      60 gcagagccgc agccgggtgg cagccagtgc gtcgagcacg actgcttcgc gctctacccg     120
ggccccgcga ccttcctcaa tgccagtcag atctgcgacg actgcggggg ccacctaatg     180
acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc ccctgcgcgg cttccagtgg gttacgggag acaacaacac cagctatagc     360
aggtgggcac ggctcgacct caatggggct ccccctctgcg gccgttgtg cgtcgctgtc     420 tccgctgctg aggccactgt gcccagcgag ccgatctggg aggagcagca gtgcgaagtg     480
aaggccgatg gcttcctctg cgagttccac ttcccagcca cctgcaggcc actggctgtg     540
gagcccggcg ccgcggctgc cgccgtctcg atcacctacg caccccgtt cgcggcccgc     600 ggagcggact ccaggcgct gccggtgggc agctccgccg cggtggctcc cctcggctta     660
cagctaatgt gcaccgcgcc gcccggagcg gtccaggggc actgggccag ggaggcgccg     720
ggcgcttggg actgcagcgt ggagaacggc gctgcgagc acgcgtgcaa tgcgatccct     780
ggggctcccc gctgccagtg cccagccggc gccgccctgc aggcagacgg gcgctcctgc     840
```

```
accgcatccg cgacgcagtc ctgcaacgac ctctgcgagc acttctgcgt tcccaacccc    900
gaccagccgg gctcctactc gtgcatgtgc gagaccggct accggctggc ggccgaccaa    960
caccggtgcg aggacgtgga tgactgcata ctggagccca gtccgtgtcc gcagcgctgt   1020
gtcaacacac agggtggctt cgagtgccac tgctacccta actacgacct ggtggacggc   1080
gagtgtgtgg agcccgtgga cccgtgcttc agagccaact gcgagtacca gtgccagccc   1140
ctgaaccaaa ctagctacct ctgcgtctgc gccgagggct cgcgcccat tcccacgag    1200 ccgcacaggt gccagatgtt ttgcaaccag actgcctgtc agccgactg cgaccccaac    1260 acccaggcta gctgtgagtg ccctgaaggc tacatcctgg acgacggttt catctgcacg   1320
gacatcgacg agtgcgaaaa cggcggcttc tgctccgggg tgtgccacaa cctccccggt   1380
accttcgagt gcatctgcgg gccccgactcg gcccttgtcc gccacattgg caccgactgt   1440
gactccggca aggtggacgg tggcgacagc ggctctggcg agccccgcc cagcccgacg   1500 cccggctcca ccttgactcc tccggccgtg gggctcgtgc attcgggc              1548
```

<210> SEQ ID NO 3
<211> LENGTH: 516
<212> TYPE: PRT
<213> ORGANISM: human

<400> SEQUENCE: 3

```
Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
                20                  25                  30

His Asp Cys Phe Ala Leu Tyr Pro Gly Pro Ala Thr Phe Leu Asn Ala
            35                  40                  45

Ser Gln Ile Cys Asp Gly Leu Arg Gly His Leu Met Thr Val Arg Ser
        50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
                100                 105                 110

Gly Asp Asn Asn Thr Ser Tyr Ser Arg Trp Ala Arg Leu Asp Leu Asn
            115                 120                 125

Gly Ala Pro Leu Cys Gly Pro Leu Cys Val Ala Val Ser Ala Ala Glu
        130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Val Ser Ile Thr
                180                 185                 190

Tyr Gly Thr Pro Phe Ala Ala Arg Gly Ala Asp Phe Gln Ala Leu Pro
            195                 200                 205

Val Gly Ser Ser Ala Ala Val Ala Pro Leu Gly Leu Gln Leu Met Cys
        210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255
```

```
Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Cys Ile Leu Glu Pro Ser Pro Cys
            325                 330                 335

Pro Gln Arg Cys Val Asn Thr Gln Gly Gly Phe Glu Cys His Cys Tyr
                340                 345                 350

Pro Asn Tyr Asp Leu Val Asp Gly Glu Cys Val Glu Pro Val Asp Pro
            355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
            405                 410                 415

Cys Asp Pro Asn Thr Gln Ala Ser Cys Glu Cys Pro Glu Gly Tyr Ile
                420                 425                 430

Leu Asp Asp Gly Phe Ile Cys Thr Asp Ile Asp Glu Cys Glu Asn Gly
            435                 440                 445

Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
            485                 490                 495

Pro Ser Pro Thr Pro Gly Ser Thr Leu Thr Pro Pro Ala Val Gly Leu
                500                 505                 510

Val His Ser Gly
            515

<210> SEQ ID NO 4
<211> LENGTH: 1548
<212> TYPE: DNA
<213> ORGANISM: human

<400> SEQUENCE: 4
atgcttgggg tcctggtcct tggcgcgctg gccctggccg gcctggggtt ccccgcaccc      60
gcagagccgc agccgggtgg cagccagtgc gtcgagcacg actgcttcgc gctctacccg     120
ggccccgcga ccttcctcaa tgccagtcag atctgcgacg actgcggggc cacctaatg     180 acagtgcgct cctcggtggc tgccgatgtc atttccttgc tactgaacgg cgacggcggc     240
gttggccgcc ggcgcctctg gatcggcctg cagctgccac ccggctgcgg cgaccccaag     300
cgcctcgggc cctgcgcgg cttccagtgg gttacgggag acaacaacac cagctatagc     360
aggtgggcac ggctcgacct caatggggct cccctctgcg gccgttgtg cgtcgctgtc     420 tccgctgctg aggccactgt gcccagcgag ccgatctggg aggagcagca gtgcgaagtg     480
aaggccgatg cttcctctg cgagttccac ttcccagcca cctgcaggcc actggctgtg     540
gagcccggcg ccgcggctgc cgccgtctcg atcacctacg gcaccccgtt cgcggcccgc     600
```

```
ggagcggact tccaggcgct gccggtgggc agctccgccg cggtggctcc cctcggctta      660
cagctaatgt gcaccgcgcc gcccggagcg gtccagggc actgggccag ggaggcgccg       720
ggcgcttggg actgcagcgt ggagaacggc ggctgcgagc acgcgtgcaa tgcgatccct      780
ggggctcccc gctgccagtg cccagccggc gccgccctgc aggcagacgg gcgctcctgc      840
accgcatccg cgacgcagtc ctgcaacgac ctctgcgagc acttctgcgt tcccaacccc      900
gaccagccgg gctcctactc gtgcatgtgc gagaccggct accggctggc ggccgaccaa      960
caccggtgcg aggacgtgga tgactgcata ctggagccca gtccgtgtcc gcagcgctgt      1020
gtcaacacac agggtggctt cgagtgccac tgctaccccta actacgacct ggtggacggc     1080
gagtgtgtgg agcccgtgga cccgtgcttc agagccaact gcgagtacca gtccagccc      1140 ctgaaccaaa ctagctacct ctgcgtctgc gccagggct tcgcgcccat tccccacgag       1200
ccgcacaggt gccagatgtt ttgcaaccag actgcctgtc cagccgactg cgaccccaac     1260
acccaggcta gctgtgagtg ccctgaaggc tacatcctgg acgacggttt catctgcacg      1320
gacatcgacg agtgcgaaaa cggcggcttc tgctccgggg tgtgccacaa cctccccggt     1380
accttcgagt gcatctgcgg gcccgactcg gcccttgccc gccacattgg caccgactgt      1440
gactccggca aggtggacgg tggcgacagc ggctctggcg agccccgcc cagcccgacg       1500 cccggctcca ccttgactcc tccggccgtg gggctcgtgc attcgggc                    1548
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5

```
aatgtggcgg gcaagggccg a                                                21
```

MEDICAMENT FOR MITIGATING CONDITIONS AND/OR SUPPRESSING ONSET OF PERIPHERAL NEUROPATHY INDUCED BY ANTI-MALIGNANT TUMOR AGENT

CROSS REFERENCE TO RELATED APPLICATIONS

This application is a Continuation of PCT International Application No. PCT/JP2019/038066, filed on Sep. 27, 2019, which claims priority under 35 U.S.C. 119(a) to Patent Application No. 2018-183447, filed in Japan on Sep. 28, 2018, all of which are hereby expressly incorporated by reference into the present application.

TECHNICAL FIELD

The present invention relates to a medicament having effects of mitigating conditions and/or suppressing onset of a peripheral neuropathy induced by an anti-malignant tumor agent.

BACKGROUND ART

In the therapeutic treatment of cancers (malignant tumors), surgery, radiotherapy, and chemotherapy are appropriately used independently or in combination. Anti-malignant tumor agents used for cancer chemotherapy among those therapies mentioned above have cytotoxicity, and cause side reactions by damaging not only cancer cells but also normal cells.

Examples of the major side reactions induced by anti-malignant tumor agents include hematotoxicity, digestive organ obstructions, and peripheral neuropathies. As the conditions of peripheral neuropathies induced by anti-malignant tumor agents, pains such as intense pain and burning pain, numbness of extremity ends, abnormal sensations such as cold hypersensitivity, dysesthesias such as anesthesia and sensory paralysis, sensory ataxia, muscle force reduction, and the like are developed. Examples of anti-malignant tumor agents that frequently cause such peripheral neuropathies include oxaliplatin (Non-patent document 1).

At present, against peripheral neuropathies induced by anti-malignant tumor agents, any effective methods for prophylactic and therapeutic treatments have not been established. There are no medicament of which indications include suppression of onset of a peripheral neuropathy induced by anti-malignant tumor agents and therapeutic treatment of the same in Japan and out of Japan. Although usefulness of intravenous administration of calcium and magnesium or glutathione have been reported for peripheral neuropathies induced by oxaliplatin, it is hardly used because, for example, such therapy further complicates cancer chemotherapy, and such substances require massive administration. In practical clinical fields, it is undesirably required to control peripheral neuropathies induced by anti-malignant tumor agents with physiotherapy, complementary therapies such as massage and acupuncture, or combination of drug therapies such as those using steroids, antidepressants, antiepileptics, opioids, and Chinese orthodox medicines (gosyajinkigan), however, effectiveness of these therapies has not been verified, and such therapies themselves frequently cause side reactions (Non-patent documents 1 and 2). Out of Japan, a guideline concerning prophylactic and therapeutic treatments of peripheral neuropathies induced by anti-malignant tumor agents has been announced (Non-patent document 3). Only duloxetine is recommended as a therapeutic agent, and any agent is not recommended as an agent for suppressing onset thereof.

Thrombomodulin is known as a substance that acts to specifically bind to thrombin so as to inhibit the blood coagulation activity of thrombin, and at the same time, significantly promote the ability of thrombin to activate Protein C, and is known to have potent blood coagulation-inhibitory activity (Non-patent document 4). A therapeutic agent for disseminated intravascular coagulation (DIC) containing human soluble thrombomodulin as an active ingredient, Recomodulin (registered trademark), has been approved as a pharmaceutical in Japan (Non-patent document 4). In addition, as intended uses of thrombomodulin, uses for severe sepsis, liver diseases, and pains accompanying hematopoietic cell transplantation have been described (Patent documents 2 to 4). As intended use of thrombomodulin, use for peripheral neuropathic pain induced by an anticancer agent has also been described (Patent document 4).

PRIOR ART REFERENCES

Patent Documents

Patent document 1: WO2013/073545
Patent document 2: Japanese Patent Unexamined Publication (KOKAI) No. 8-3065
Patent document 3: Japanese Patent Unexamined Publication (KOKAI) No. 2011-178687
Patent document 4: WO2013/179910

Non-Patent Documents

Non-patent document 1: Folia Pharmacologica Japonica (Nippon Yakurigaku Zasshi), 2010, 136:275-279
Non-patent document 2: EMBO Journal, 1987, 6:1891-1897
Non-patent document 3: JOURNAL OF CLINICAL ONCOLOGY, 2014, Hershman et al., Prevention and Management of Chemotherapy-Induced Peripheral Neuropathy in Survivors of Adult Cancers: American Society of Clinical Oncology Clinical Practice Guideline
Non-patent document 4: Package insert of Recomodulin (registered trademark)

SUMMARY OF THE INVENTION

Object to be Achieved by the Invention

An object of present invention is to provide an effective and safe medicament having effects for mitigating conditions and/or suppressing onset of a peripheral neuropathy induced by administration of the anti-malignant tumor agent, oxaliplatin, used in an anti-malignant tumor treatment with oxaliplatin in a human cancer patient receiving the treatment.

Means for Achieving the Object

It is known that thrombomodulin is effective for a peripheral neuropathic pain induced by an anticancer agent (Patent document 4). However, Patent document 4 only qualitatively describes that intraperitoneal administration of thrombomodulin over seven contiguous days was effective for a peripheral neuropathic pain that originated in use of an anticancer agent in a rat model in which peripheral neuropathy was developed by administering the anticancer agent multiple times. Patent document 4 also exemplifies administering TMD123 (e.g., Recomodulin as registered trademark) 3 times in each course of treatment, i.e., immediately before, during, and immediately after the administration of the anticancer agent. Although Patent document 4 further generally describes administration frequency of thrombomodulin, it does not describe at all administering thrombomodulin once on the first day of each cycle of the anti-malignant tumor treatment with oxaliplatin. In addition, it reports absolutely no information concerning administration method or dose of thrombomodulin with which thrombomodulin could be effectively and safely administered to a human cancer patient receiving the anti-malignant tumor treatment with oxaliplatin for suppressing onset of a peripheral neuropathy induced by the anti-malignant tumor agent.

The inventors of the present invention conducted various researches in order to achieve the aforementioned object of effectively and safely mitigating conditions and/or suppressing onset of a peripheral neuropathy caused in a human cancer patient receiving anti-malignant tumor treatment with oxaliplatin. As a result, they unexpectedly found that the aforementioned object can be achieved by single administration of 0.06 mg/kg of thrombomodulin on the first day of each cycle of the anti-malignant tumor treatment with oxaliplatin, and accomplished the present invention.

The present invention can be thus embodied, for example, as follows.

[1] A medicament for mitigating conditions and/or suppressing onset of a peripheral neuropathy induced by an anti-malignant tumor agent in a human cancer patient receiving an anti-malignant tumor treatment with oxaliplatin, wherein the anti-malignant tumor treatment comprises the step of repeating a single cycle comprising intravenous administration of oxaliplatin to the human cancer patient and following drug withdrawal, and the medicament contains thrombomodulin for intravenously administering 0.06 mg/kg of thrombomodulin once per said single cycle of the anti-malignant tumor treatment on the first day of each said cycle as an active ingredient.

[1-2] The medicament for mitigating conditions and/or suppressing onset of a peripheral neuropathy induced by an anti-malignant tumor agent in a human cancer patient receiving an anti-malignant tumor treatment with oxaliplatin according to [1] mentioned above, wherein the anti-malignant tumor treatment comprises the step of repeating a single cycle comprising one to six times of intravenous administration of oxaliplatin to the human cancer patient and following drug withdrawal for at least 6 days, and the medicament contains thrombomodulin for intravenously administering 0.06 mg/kg of thrombomodulin once per said single cycle of the anti-malignant tumor treatment on the first day of each said cycle as an active ingredient.

[1-3] The medicament according to [1] mentioned above, wherein the cycle of the anti-malignant tumor treatment is repeated 1 to 12 times.

[1-4] The medicament according to [1] or [1-2] mentioned above, wherein the cycle of the anti-malignant tumor treatment is repeated at least 8 times.

[1-5] The medicament according to [1] or [1-2] mentioned above, wherein the cycle of the anti-malignant tumor treatment is repeated at least 12 times.

[1-6] A medicament for mitigating conditions and/or suppressing onset of a peripheral neuropathy induced by oxaliplatin in a treatment repeating a single cycle comprising intravenous administration of oxaliplatin to a human cancer patient and following drug withdrawal, which contains thrombomodulin for intravenously administering 0.06 mg/kg of thrombomodulin once per said single cycle of the treatment on the first day of each said cycle as an active ingredient.

[2] The medicament according to any one of [1] to [1-6] mentioned above, which is for suppressing reduction of the total dose of oxaliplatin in the anti-malignant tumor treatment.

When the cited item numbers are indicated as a range like [1] to [1-6] as mentioned above, and an item indicated with an item number having a sub-number such as [1-2] is included in the range, it means that the item indicated with the item number having a sub-number such as [1-2] is also cited. This rule also holds for the following descriptions.

[3] The medicament according to [1] or [2] mentioned above, wherein the anti-malignant tumor treatment with oxaliplatin comprises the step of repeating a single cycle comprising once per day of intravenous administration of 50 to 150 mg/m$^2$ (body surface area) of oxaliplatin to the human cancer patient for 1 to 3 days, and following drug withdrawal for at least 13 days.

[3-2] The medicament according to [1] or [2] mentioned above, wherein the anti-malignant tumor treatment with oxaliplatin comprises the step of repeating a single cycle comprising once a day of intravenous administration of 50 to 150 mg/m$^2$ (body surface area) of oxaliplatin to the human cancer patient for 1 day, and following drug withdrawal for 13 to 24 days.

[3-3] The medicament according to [1] or [2] mentioned above, wherein the anti-malignant tumor treatment with oxaliplatin comprises the step of repeating a single cycle comprising once a day of intravenous administration of 80 to 140 mg/m$^2$ (body surface area) of oxaliplatin to the human cancer patient for 1 day, and following drug withdrawal for at least 13 days. [3-4] The medicament according to [1] or [2] mentioned above, wherein the anti-malignant tumor treatment with oxaliplatin comprises the step of repeating a single cycle comprising once a day of intravenous administration of 80 to 90 mg/m$^2$ (body surface area) of oxaliplatin to the human cancer patient for 1 day, and following drug withdrawal for at least 13 days.

[3-5] The medicament according to [1] or [2] mentioned above, wherein the anti-malignant tumor treatment with oxaliplatin comprises the step of repeating a single cycle comprising once a day of intravenous administration of 120 to 140 mg/m$^2$ (body surface area) of oxaliplatin to the human cancer patient for 1 day, and following drug withdrawal for at least 20 days.

[3-6] The medicament according to any one of [3] to [3-5] mentioned above, wherein the cycle of the anti-malignant tumor treatment is repeated 1 to 12 times.

[3-7] The medicament according to any one of [3] to [3-5] mentioned above, wherein the cycle of the anti-malignant tumor treatment is repeated at least 8 times.

[3-8] The medicament according to any one of [3] to [3-5] mentioned above, wherein the cycle of the anti-malignant tumor treatment is repeated at least 12 times.

[4] The medicament according to any one of [1] to [3-4], [3-6], and [3-7] mentioned above, wherein oxaliplatin is administered according to the FOLFOX therapy.

[5] The medicament according to any one of [1] to [4] mentioned above, wherein the administration of thrombomodulin is started before start of the administration of oxaliplatin.

[5-2] The medicament according to any one of [1] to [4] mentioned above, wherein the administration of thrombomodulin is started 30 minutes to 3 hours before the start of the administration oxaliplatin.

[6] The medicament according to any one of [1] to [5-2] mentioned above, which is administered to a cancer patient suffering from one or more kinds of cancers selected from the group consisting of large bowel cancer, pancreatic cancer, and gastric cancer.

[7] The medicament according to any one of [1] to [6] mentioned above, wherein the peripheral neuropathy is motor peripheral neuropathy or sensory peripheral neuropathy.

[8] The medicament according to any one of [1] to [7] mentioned above, wherein the thrombomodulin is soluble thrombomodulin.

[9] The medicament according to any one of [1] to [7] mentioned above, wherein the thrombomodulin is human thrombomodulin.

[10] The medicament according to any one of [1] to [7] mentioned above, wherein the thrombomodulin is a peptide obtainable from a transformed cell prepared by transfecting a host cell with a DNA coding for the amino acid sequence of (i-1) or (i-2) mentioned below (the peptide obtainable from a DNA coding for the amino acid sequence of (i-2) has the thrombomodulin activities);
(i-1) the amino acid sequence of SEQ ID NO: 1 or 3, or
(i-2) the amino acid sequence of (i-1) mentioned above, further including substitution, deletion or addition of one or more amino acid residues.

[10-2] The medicament according to any one of [1] to [7] mentioned above, wherein the thrombomodulin is a peptide obtainable from a transformed cell prepared by transfecting a host cell with a DNA coding for the amino acid sequence of (i-1) mentioned below;
(i-1) the amino acid sequence of SEQ ID NO: 1 or 3.

[11] The medicament according to any one of [1] to [7] mentioned above, wherein the thrombomodulin is a peptide containing the amino acid sequence of (i-1) or (i-2) mentioned below, and the peptide is a peptide having the thrombomodulin activities;
(i-1) the amino acid sequence of the positions 19 to 516 in the amino acid sequence of SEQ ID NO: 1 or 3, or
(i-2) the amino acid sequence of (i-1) mentioned above, further including substitution, deletion or addition of one or more amino acid residues.

[11-2] The medicament according to any one of [1] to [7] mentioned above, wherein the thrombomodulin is a peptide containing the amino acid sequence of (i-1) mentioned below, and the peptide is a peptide having the thrombomodulin activities;
(i-1) the amino acid sequence of the positions 19 to 516 in the amino acid sequence of SEQ ID NO: 1 or 3.

[12] The medicament according to any one of [1] to [9] mentioned above, wherein the thrombomodulin is Thrombomodulin alfa (genetical recombination).

[13] Use of thrombomodulin for manufacture of a medicament for mitigating conditions and/or suppressing onset of a peripheral neuropathy induced by an anti-malignant tumor agent in a human cancer patient receiving an anti-malignant tumor treatment with oxaliplatin, wherein the anti-malignant tumor treatment comprises the step of repeating a single cycle comprising intravenous administration of oxaliplatin to the human cancer patient and following drug withdrawal, and the use is for intravenously administering 0.06 mg/kg of thrombomodulin once per said single cycle of the anti-malignant tumor treatment on the first day of each said cycle.

[13-2] Use according to [13] mentioned above, which has one or more of the characteristics defined in [1] to [12] mentioned above.

[14] Thrombomodulin for mitigating conditions and/or suppressing onset of a peripheral neuropathy induced by an anti-malignant tumor agent in a human cancer patient receiving an anti-malignant tumor treatment with oxaliplatin, wherein the anti-malignant tumor treatment comprises the step of repeating a single cycle comprising intravenous administration of oxaliplatin to the human cancer patient and following drug withdrawal, and the thrombomodulin is for intravenously administering 0.06 mg/kg of thrombomodulin once per said single cycle of the anti-malignant tumor treatment on the first day of each said cycle.

[14-2] The thrombomodulin according to [14] mentioned above, which has one or more of the characteristics defined in [1] to [12] mentioned above.

[15] A method for mitigating conditions and/or suppressing onset of a peripheral neuropathy induced by an anti-malignant tumor agent in a human cancer patient receiving an anti-malignant tumor treatment with oxaliplatin, wherein the method comprises the step of administering thrombomodulin to the human cancer patient, the anti-malignant tumor treatment comprises the step of repeating a single cycle comprising intravenous administration of oxaliplatin to the human cancer patient and following drug withdrawal, and the method is for intravenously administering 0.06 mg/kg of thrombomodulin once per said single cycle of the anti-malignant tumor treatment on the first day of each said cycle.

[15-2] The method according to [15] mentioned above, which has one or more of the characteristics defined in [1] to [12] mentioned above.

Effect of the Invention

The present invention enables safe and effective mitigation of conditions and/or suppression of onset of a peripheral neuropathy induced by administration of an anti-malignant tumor agent in a human cancer patient receiving a treatment with the anti-malignant tumor agent.

BRIEF DESCRIPTION OF THE DRAWINGS

FIG. 1 shows the results of investigation of the prophylactic effect of seven times of administration of ART-123 on hyperalgesia (decrease of pressure pain threshold) caused in rats by oxaliplatin administration. Oxaliplatin (6 mg/kg) was intraperitoneally administered at the time indicated with the white arrow for all the cases.
Arrow: administration of ART-123 or medium
●: Solvent administration group
Δ: 0.3 mg/kg ART-123 administration group
□: 1 mg/kg ART-123 administration group
○: 10 mg/kg ART-123 administration group
**: $p<0.005$ (comparison with solvent administration group)
: $p<0.01$ (comparison with solvent administration group on the day before the day of oxaliplatin administration)

FIG. 2 shows the results of investigation of the prophylactic effect of one, two, or three times of administration of ART-123 on hyperalgesia (decrease of pressure pain threshold) caused in rats by oxaliplatin administration. Oxaliplatin (6 mg/kg) was intraperitoneally administered at the time indicated with the white arrow for all the cases.

Solid line arrow: Administration of 1 mg/kg ART-123
Broken line arrow: Administration of solvent
●: Medium administration group
△: Single ART-123 administration group
□: Double ART-123 administration group
○: Triple ART-123 administration group
n.s.: No significant difference
*: $p<0.025$ (comparison with medium administration group)
**: $p<0.005$ (comparison with medium administration group)
$p<0.01$ (comparison with medium administration group on the day before the day of oxaliplatin administration)

MODES FOR CARRYING OUT THE INVENTION

Hereafter, several preferred embodiments of the present invention (preferred modes for carrying out the invention, henceforth also referred to as "embodiments" in the specification) will be specifically explained. However, the scope of the present invention is not limited to the specific embodiments explained below.

For one embodiment, as the thrombomodulin, a peptide containing at least the sequence of the positions 19 to 516 of the sequence of SEQ ID NO: 1 or 3, or a mutated homologous sequence thereof, and having the thrombomodulin activities mentioned below can be exemplified. For another embodiment, a peptide containing at least the sequence of the positions 19 to 516 of the sequence of SEQ ID NO: 1 can be exemplified. For still another embodiment, a peptide containing a mutated homologous sequence of the sequence of SEQ ID NO: 1 can be exemplified.

Examples of the mutated homologous sequence include a peptide sequence having the amino acid sequence of the corresponding peptide, which may further include substitution, deletion or addition of one or more amino acid residues. The number of amino acid residues that may be substituted, deleted, or added may be, for example, 1 to 40, preferably 1 to 20, more preferably 1 to 10, further preferably 1 to 5, particularly preferably 1 to 3. Examples of the mutated homologous sequence also include a peptide sequence having a homology higher than a certain level to the amino acid sequence of the corresponding peptide. The homology higher than a certain level is, for example, a homology of 80% or higher, preferably 85% or higher, more preferably 90% or higher, further preferably 95% or higher, particularly preferably 98% or higher.

As the thrombomodulin activities, actions of (1) selectively binding to thrombin (2) to promote activation of Protein C by thrombin can be mentioned. (3) An action of extending thrombin clotting time, (4) an action of suppressing platelet aggregation induced by thrombin, and (5) anti-inflammatory action can be also exemplified. As the thrombomodulin activities, for example, thrombomodulin has the actions of (1) and (2) mentioned above, or the actions of (1) to (4) mentioned above. For another embodiment, thrombomodulin has all the actions of (1) to (5).

The action of thrombomodulin to bind with thrombin can be confirmed by the study methods described in various known publications such as Thrombosis and Haemostasis, 1993, 70(3)418-422 and The Journal of Biological Chemistry, 1989, 264, 9, pp. 4872-4876. As for the action of promoting activation of Protein C by thrombin, degree of the activity of promoting the activation of Protein C by thrombin or presence or absence of the action can be easily confirmed by the study methods clearly described in various known publications including, for example, Japanese Patent Unexamined Publication (KOKAD No. 64-6219. Further, the action of extending thrombin clotting time, and/or the action of suppressing platelet aggregation induced by thrombin can be similarly and easily confirmed. Furthermore, the anti-inflammatory action can also be confirmed by the study methods described in various known publications including, for example, Blood, 2008, 112:3361-3670 and The Journal of Clinical Investigation, 2005, 115, 5:1267-1274.

For one embodiment, as the thrombomodulin, a peptide consisting of the sequence of the positions 19 to 516, positions 19 to 515, positions 17 to 516, or positions 17 to 515 in the sequence of SEQ ID NO: 1 or 3 can be exemplified. The thrombomodulin may be a mixture of the peptides consisting of the sequence of the positions 19 to 516, positions 19 to 515, positions 17 to 516, or positions 17 to 515 of the sequence of SEQ ID NO: 1 or 3.

For one embodiment, although the thrombomodulin is not particularly limited so long as it is the thrombomodulin described above, soluble thrombomodulin can be exemplified. For another embodiment, human thrombomodulin can be exemplified. For still another embodiment, human soluble thrombomodulin can be exemplified. For another embodiment, Thrombomodulin alfa (genetical recombination) can be exemplified. Thrombomodulin alfa (genetical recombination) is an active ingredient of Recomodulin (registered trademark), which is approved as a pharmaceutical in Japan. Thrombomodulin alfa (genetical recombination) is also called ART-123.

Examples of the soluble thrombomodulin include thrombomodulin soluble in water in the absence of surfactant. The solubility of the soluble thrombomodulin in water such as distilled water used for injection (in the absence of a surfactant such as Triton X-100 or polidocanol, and generally around the neutral pH range) is preferably, for example, 1 mg/mL or higher or 10 mg/mL or higher; preferably 15 mg/mL or higher or 17 mg/mL or higher; more preferably 20 mg/mL or higher, 25 mg/mL or higher, or 30 mg/mL or higher; particularly preferably 60 mg/mL or higher. In some cases, the solubility is, for example, 80 mg/mL or higher, or 100 mg/mL or higher. For determining whether or not a soluble thrombomodulin is successfully dissolved, it is understood that, when the soluble thrombomodulin is dissolved in water and the solution is observed by visual inspection, for example, just under a white light at a position corresponding to an illumination of approximately 1000 luxes, clear appearance of the solution and the absence of apparently observable insoluble substances is served as simple criteria. It can also be confirmed by observing the presence or absence of any residue after filtration of the solution.

The molecular weight of the thrombomodulin is preferably 100,000 or smaller, more preferably 90,000 or smaller, still more preferably 80,000 or smaller, most preferably 70,000 or smaller, and the molecular weight is preferably 50,000 or larger, most preferably 60,000 or larger. The molecular weight of the soluble thrombomodulin can be easily measured by ordinary methods for measuring molecular weight of protein. Measurement by mass spectrometry is preferred, and MALDI-TOF-MS method is more preferred. For obtaining a soluble thrombomodulin having a molecular weight within a desired range, a soluble thrombomodulin, which is obtained by culturing a transformant cell prepared by transfecting a host cell with a DNA encoding the soluble thrombomodulin using a vector, can be subjected to fractionation using column chromatography or the like as described later.

As described below, these thrombomodulins can be obtained from transformant cells prepared by transfecting host cells with a DNA encoding any of these peptides (specifically, the nucleotide sequences of SEQ ID NOS: 2, 4, and the like) by using a vector.

It is sufficient that these peptides only have the aforementioned amino acid sequences, and a sugar chain may be attached or not attached, which is not particularly limited. In gene manipulation techniques, a type of a sugar chain, a position to which a sugar chain is added, and a level of addition thereof differ depending on a type of host cells used, and any techniques may be used. As for binding position of a sugar chain and a type thereof, facts described in Japanese Patent Unexamined Publication (KOKAI) No. 11-341990 are known, and the thrombomodulins used for one embodiment may be added with the same sugar chain at the same position. Two types of N-linked sugar chains, those of fucosyl biantennary type and fucosyl triantennary type, may bind to the thrombomodulin in one embodiment, and ratio thereof is, for example, 100:0 to 60:40, preferably 95:5 to 60:40, more preferably 90:10 to 70:30. The ratio of these sugar chains can be measured on a two-dimensional sugar chain map described in Biochemical Experimental Methods, Vol. 23, Methods of Researches on Glycoprotein Sugar Chains, Japan Scientific Societies Press (1990), and the like. Furthermore, when a sugar composition of the thrombomodulin for one embodiment is examined, neutral saccharides, aminosaccharides, and sialic acid are detected, of which content may be, each independently, for example, 1 to 30%, preferably 2 to 20%, more preferably 5 to 10%, in terms of weight ratio based on the protein content. The sugar contents can be measured by the methods described in Lecture of New Biochemical Experiments, Vol. 3, Sugar I, Glycoprotein (Book 1), Tokyo Kagaku Dojin (1990) (neutral saccharides: phenol-sulfuric acid method, aminosaccharides: Elson-Morgan method, sialic acid: periodic acid-resorcinol method).

Although the method for obtaining thrombomodulin is not limited to obtaining it by genetic manipulation as described later, when the thrombomodulin is obtained by gene manipulation, as a signal sequence that can be used for expression, a nucleotide sequence encoding the amino acid sequence of the positions 1 to 18 in the sequence of SEQ ID NO: 1, and a nucleotide sequence encoding the amino acid sequence of the positions 1 to 16 in the sequence of SEQ ID NO: 1 can be used, and other known signal sequences such as the signal sequence of human tissue plasminogen activator can also be used (International Publication WO88/9811).

When a DNA sequence encoding thrombomodulin is introduced into a host cell, examples of preferred methods include a method of incorporating a DNA sequence encoding thrombomodulin into, preferably, a vector, more preferably an expression vector capable of being expressed in animal cells, and then introducing the DNA with the vector. An expression vector is a DNA molecule that is constituted with a promoter sequence, a sequence for adding a ribosome binding site to mRNA, a DNA sequence encoding a protein to be expressed, a splicing signal, a terminator sequence for transcription termination, a replication origin sequence, and the like. Examples of preferred animal cell expression vector include pSV2-X reported by Mulligan R. C. et al. (Proc. Natl. Acad. Sci. U.S.A., 1981, 78, 2072-2076); pBP69T (69-6) reported by Howley P. M. et al. (Methods in Emzymology, 1983, 101, 387-402, Academic Press), and the like. Further, there is also another preferred embodiment in which DNA is introduced into an expression vector expressible in a microorganism.

Examples of host cell that can be used in production of such peptides as mentioned above include animal cells. Examples of the animal cells include Chinese hamster ovary (CHO) cells, COS-1 cells, COS-7 cells, VERO (ATCC CCL-81) cells, BHK cells, canine kidney-derived MDCK cells, hamster AV-12-664 cells, and the like. In addition, examples of host cell derived from human include HeLa cells, WI38 cells, human 293 cells, and PER.C6 cells. Of these cells, CHO cells are very common and preferred, and among the CHO cells, dihydrofolate reductase (DHFR)-deficient CHO cells are more preferred.

In a gene manipulation process or a peptide production process, microorganisms such as *Escherichia coli* are also often used. A host-vector system suitable for each process is preferably used, and an appropriate vector system can also be selected for the aforementioned host cells. A thrombomodulin gene used in a genetic recombination technique has been cloned. Examples of production of thrombomodulin by such a gene recombination technique have been disclosed, and further, methods for purifying thrombomodulin to obtain a purified product thereof are also known (Japanese Patent Unexamined Publication (KOKAI) Nos. 64-6219, 2-255699, 5-213998, 5-310787, 7-155176; and J. Biol. Chem., 1989, 264:10351-10353). Therefore, the thrombomodulin used for one embodiment can be produced by using the methods described in the aforementioned reports, or by similar methods. For example, Japanese Patent Unexamined Publication (KOKAI) No. 64-6219 discloses the *Escherichia coli* K-12 strain DH5 (ATCC Accession No. 67283) containing a plasmid pSV2TMJ2 that contains a DNA encoding the full-length thrombomodulin. This strain re-deposited at the National Institute of Bioscience and Human-Technology (currently Independent Administrative Institution, National Institute of Advanced Industrial Science and Technology, International Patent Organism Depositary) (*Escherichia coli* DH5/pSV2TMJ2) (FERM BP-5570) can also be used. The thrombomodulin used for one embodiment can be prepared by a known gene manipulation technique using a DNA encoding the full-length thrombomodulin as a starting material.

For one embodiment, the thrombomodulin may be prepared by a conventionally known method or a similar method. For example, the aforementioned method of Yamamoto et al. (Japanese Patent Unexamined Publication (KOKAI) No. 64-6219) or the method described in Japanese Patent Unexamined Publication (KOKAI) No. 5-213998 can be referred to. Specifically, for example, a DNA encoding the amino acid sequence of SEQ ID NO: 1 is prepared from a human-derived thrombomodulin gene by a gene manipulation technique, and may be further modified as required. For such modification, in order to obtain a DNA encoding the amino acid sequence of SEQ ID NO: 3 (which specifically consists of the nucleotide sequence of SEQ ID NO: 4), codons encoding the amino acid at the position 473 in the amino acid sequence of SEQ ID NO: 1 (in particular, the nucleotide at the position 1418 in the sequence of SEQ ID NO: 2) are mutated by site-directed mutagenesis according to the method described by Zoller M. J. et al. (Method in Enzymology, 1983, 100:468-500, Academic Press). For example, by using a synthetic DNA for mutation having the nucleotide sequence of SEQ ID NO: 5, the nucleotide Tat the position 1418 in the sequence of SEQ ID NO: 2 may be converted to the nucleotide C to obtain a mutated DNA.

The DNA prepared as described above is incorporated into, for example, Chinese hamster ovary (CHO) cells to obtain transformant cells. Such cells are subjected to appropriate selection, and thrombomodulin purified by a known method can be produced from a culture solution obtained by culturing a selected cell. As described above, the DNA (SEQ ID NO: 2) encoding the amino acid sequence of SEQ ID NO: 1 is preferably transfected into the aforementioned host cell.

The method for producing thrombomodulin for one embodiment is not limited to the aforementioned method. For example, it is also possible to extract and purify the thrombomodulin from urine, blood, other body fluids and the like, or extract and purify the thrombomodulin from a tissue producing thrombomodulin or a culture of the aforementioned tissue and the like. Further, the thrombomodulin may be further subjected to a cleavage treatment using a protease, as required.

For the culture of the aforementioned transformant cell, a medium used for ordinary cell culture may be used, and it is preferable to culture the transformant cell in various kinds of media in advance to choose an optimal medium. For example, a known medium such as MEM medium, DMEM medium, and 199 medium may be used as a base medium, and a further improved medium or a medium added with supplements for various media may be used. Examples of the culture method include serum culture, in which culture is performed in a medium containing blood serum, and serum-free culture, in which culture is performed in a medium not containing blood serum. Although the culture method is not particularly limited, the serum-free culture is preferred.

When serum is added to a medium in the case of the serum culture, bovine serum is preferred. Examples of bovine serum include fetal bovine serum, neonate bovine serum, calf bovine serum, adult bovine serum, and the like, and any of these examples may be used so far that the serum is suitable for the cell culture. As the serum-free medium used in the serum-free culture, commercially available media can be used. Serum-free media suitable for various cells are marketed, and for example, for the CHO cell, CD-CHO, CHO-S-SFMII and CHO-III-PFM are sold by Invitrogen, and IS CHO, IS CHO-CD medium, and the like are sold by Irvine Scientific. These media may be used without any treatment, or they may be improved or added with supplements and used. Examples of the serum-free medium further include the DMEM medium containing 5 mg/L each of insulin, transferrin, and selenious acid. As described above, the medium is not particularly limited so far that the medium can be used to produce the thrombomodulin for one embodiment. The culture method is not particularly limited, and any of batch culture, repetitive batch culture, fed-batch culture, perfusion culture, and the like may be used.

When the thrombomodulin used for one embodiment is prepared by the aforementioned cell culture method, diversity may be observed in the N-terminus amino acid due to posttranslational modification of the protein. For example, the amino acid of the position 17, 18, 19 or 22 in the sequence of SEQ ID NO: 1 may serve as the N-terminus amino acid. Further, for example, the N-terminus amino acid may be modified so that the glutamic acid at the position 22 is changed to pyroglutamic acid. It is preferred that the amino acid of the position 17 or 19 serves as the N-terminus amino acid, and it is more preferred that the amino acid of the position 19 serves as the N-terminus amino acid. Further, there is also another preferred embodiment in which the amino acid of the position 17 serves as the N-terminus amino acid. As for the modification, diversity and the like mentioned above, similar examples can be mentioned for the sequence of SEQ ID NO: 3.

Further, when the soluble thrombomodulin is prepared by using a DNA having the nucleotide sequence of SEQ ID NO: 2, diversity of the C-terminus amino acid may be observed, and a peptide shorter by one amino acid residue may be produced. Specifically, the C-terminus amino acid may be modified so that the amino acid of the position 515 serves as the C-terminus amino acid, and further the position 515 is amidated. Further, a peptide shorter by two amino acid residues may be produced. Specifically, the amino acid of the position 514 may serve as the C-terminus amino acid. Therefore, any of peptides having significant diversity of the N-terminus amino acid and C-terminus amino acid, or a mixture of them may be produced. It is preferred that the amino acid of the position 515 or the amino acid of the position 516 serves as the C-terminus amino acid, and it is more preferred that the amino acid of the position 516 serves as the C-terminus amino acid. Further, there is also another embodiment in which the amino acid of the position 514 preferably serves as the C-terminus amino acid. Concerning the modification, diversity and the like described above, the same shall apply to a DNA having the nucleotide sequence of SEQ ID NO: 4.

The thrombomodulin obtained by the method described above may be a mixture of peptides having diversity in the N-terminus and C-terminus amino acids. Specific examples include a mixture of peptides having the sequences of the positions 19 to 516, positions 19 to 515, positions 19 to 514, positions 17 to 516, positions 17 to 515, and positions 17 to 514 in the sequence of SEQ ID NO: 1.

Then, isolation and purification of thrombomodulin from a culture supernatant or culture obtained as described above can be carried out by known methods [*Tanpakushitsu/Koso no Kiso Jikken Ho* (Fundamental Experimental Methods for Proteins and Enzymes), 1981, edited by Takeichi Horio]. For example, it is preferable to use ion exchange chromatography or adsorption chromatography, which utilizes an interaction between thrombomodulin and a chromatographic carrier on which functional groups having a charge opposite to that of thrombomodulin are immobilized. Another preferred example is affinity chromatography utilizing specific affinity with thrombomodulin. Preferred examples of adsorbent include thrombin that is a ligand of thrombomodulin and an anti-thrombomodulin antibody. As the antibody, anti-thrombomodulin antibodies having appropriate properties or recognizing appropriate epitopes can be used. Examples include, for example, those described in Japanese Patent Publication (KOKOKU) No. 5-42920, Japanese Patent Unexamined Publication (KOKAI) Nos. 64-45398 and 6-205692 and the like. Other examples include gel filtration chromatography and ultrafiltration, which utilize the molecular size of thrombomodulin. Other examples further include hydrophobic chromatography that utilizes hydrophobic bond between a chromatographic carrier on which hydrophobic groups are immobilized, and a hydrophobic portion of thrombomodulin. Furthermore, hydroxyapatite may be used as a carrier in adsorption chromatography, of which examples include, for example, those described in Japanese Patent Unexamined Publication (KOKAI) No. 9-110900. These means may be used in combination, as required. Although degree of purification can be selected depending on a purpose of use and the like, it is desirable to purify thrombomodulin until a single band is obtained as a result of electrophoresis, preferably SDS-PAGE, or a single peak is obtained as a result of gel filtration HPLC or reverse phase HPLC of the isolated and purified product. It should of course be understood that, when two or more types of thrombomodulins are used, it is preferred that only the bands of the thrombomodulins are substantially obtained, and it is not required to obtain one single band.

Specific examples of the purification method for one embodiment include a purification method using the thrombomodulin activities as a criterion, for example, a purification method comprising roughly purifying a culture supernatant or a culture product with an ion exchange column Q-Sepharose Fast Flow to collect a fraction having the thrombomodulin activities; then purifying the fraction with an affinity column, DIP-thrombin-agarose (diisopropylphosphorylthrombin agarose) column, as the main purification step to recover a fraction having potent thrombomodulin activities; then concentrating the recovered fraction and followed by gel filtration to obtain a thrombomodulin active fraction as a purified product (Gomi K. et al., Blood, 1990, 75: 1396-1399). An example of the thrombomodulin activities used as the criterion is an activity of promoting the activation of Protein C by thrombin. Other preferred examples of the purification method will be exemplified below.

An appropriate ion exchange resin having good adsorptive condition for thrombomodulin is selected, and purification by ion exchange chromatography is performed. A particularly preferred example is a method comprising the use of Q-Sepharose Fast Flow equilibrated with a 0.02 mol/L Tris-HCl buffer (pH 7.4) containing 0.18 mol/L NaCl. After washing as required, elution can be performed with a 0.02 mol/L Tris-HCl buffer (pH 7.4) containing 0.3 mol/L NaCl, for example, to obtain thrombomodulin as a roughly purified product.

Then, for example, a substance having specific affinity for thrombomodulin can be immobilized on a resin, and affinity chromatography purification can be performed. Preferred examples include use of a DIP-thrombin-agarose column and use of an anti-thrombomodulin monoclonal antibody column. In the case of the DIP-thrombin-agarose column, the column is equilibrated beforehand with a 20 mmol/L Tris-HCl buffer (pH 7.4) containing 100 mmol/L NaCl and 0.5 mmol/L calcium chloride, and the aforementioned roughly purified product can be then charged on the column, washed as required, and then eluted with, for example, a 20 mmol/L Tris-HCl buffer (pH 7.4) containing 1.0 mol/L NaCl and 0.5 mmol/L calcium chloride to obtain thrombomodulin as a purified product. In the case of the anti-thrombomodulin monoclonal antibody column, an example of the method comprises: contacting an anti-thrombomodulin monoclonal antibody solution in a 0.1 mol/L NaHCO$_3$ buffer (pH 8.3) containing 0.5 mol/L NaCl with Sepharose 4FF (GE Health Care Biosciences) activated with CNBr beforehand to obtain the resin Sepharose 4FF coupled with the anti-thrombomodulin monoclonal antibodies, equilibrating the resin filled in a column beforehand with, for example, a 20 mmol/L phosphate buffer (pH 7.3) containing 0.3 mol/L NaCl, washing the resin as required, and then performing elution with, for example, a 100 mmol/L glycine-HCl buffer (pH 3.0) containing 0.3 mol/L NaCl. An effluent may be neutralized with an appropriate buffer to obtain a product as a purified product.

Subsequently, the obtained purified product is adjusted to pH 3.5, and then charged on a cation exchanger, preferably SP-Sepharose FF (GE Health Care Biosciences) as a strong cation exchanger, equilibrated with a 100 mmol/L glycine-HCl buffer (pH 3.5) containing 0.3 mol/L NaCl, and washing is performed with the same buffer to obtain a non-adsorptive fraction. The resulting fraction is neutralized with an appropriate buffer to obtain a highly purified product. This product is preferably concentrated by ultrafiltration.

Further, it is also preferable to exchange the buffer by gel filtration. For example, a highly purified product concentrated by ultrafiltration can be charged on a Sephacryl S-300 column or S-200 column equilibrated with a 20 mmol/L phosphate buffer (pH 7.3) containing 50 mmol/L NaCl, and then developed for fractionation with a 20 mmol/L phosphate buffer (pH 7.3) containing 50 mmol/L NaCl. The activity for promoting the activation of Protein C by thrombin can be confirmed to collect an active fraction and thereby obtain a buffer-exchanged highly purified product. In order to improve safety, a highly purified product obtained as described above is preferably filtered through an appropriate filter for eliminating viruses such as Planova 15N (Asahi Kasei Medical Co., Ltd.), and then the resultant can be concentrated by ultrafiltration to a desired concentration. Finally, the product is preferably filtered through an aseptic filtration membrane.

For one embodiment, as the "peripheral neuropathy induced by an anti-malignant tumor agent", a peripheral neuropathy induced by administration of such an anti-malignant tumor agent as exemplified above to a human cancer patient can be exemplified. In this specification, it may also be called "chemotherapy-induced peripheral neuropathy".

For one embodiment, as the "anti-malignant tumor agent", a drug that exhibits certain clinical usefulness in a malignant tumor patient, such as suppression of growth or metastasis of malignant tumor lesion, prolongation of life, and control of symptoms, can be exemplified. Specifically, oxaliplatin can be exemplified. For one embodiment, as the peripheral neuropathy induced by an anti-malignant tumor agent, peripheral neuropathies induced by oxaliplatin can be exemplified.

Oxaliplatin is an anti-malignant tumor agent that inhibits the metabolism of nucleic acids, and is classified into platinum agent. Oxaliplatin is the active ingredient of ELPLAT (registered trademark), which has been approved as a pharmaceutical in Japan. A peripheral neuropathy induced by an anti-malignant tumor agent in a human cancer patient receiving an anti-malignant tumor treatment with oxaliplatin may be called oxaliplatin-induced peripheral neuropathy.

For one embodiment, as the peripheral neuropathy, numbness of extremities, pain of extremities, reduction of deep tendon reflection, reduction of muscle force, allodynia, hyperalgesia, and motor dysfunction can be exemplified. Examples of the symptoms of peripheral neuropathy also include pains such as intense pain and burning pain, numbness of extremity ends, abnormal sensation such as burning sensation, hyperesthesia such as cold hypersensitivity, dysesthesia such as anesthesia, sensory paralysis, and discomfort, sensory ataxia, and reduction of muscle force. The peripheral neuropathy can be roughly classified into three types, motor peripheral neuropathy, sensory peripheral neuropathy, and autonomic peripheral neuropathy, but it is not limited to these. Examples of motor peripheral neuropathy include inflammation or degeneration of peripheral motor nerves, examples of sensory peripheral neuropathy include inflammation or degeneration of peripheral sensory nerves, and examples of autonomic peripheral neuropathy include inflammation or degeneration of peripheral autonomic nerves.

Examples of the method for evaluating effects for suppressing onset and/or mitigating conditions of peripheral neuropathy induced by an anti-malignant tumor agent include evaluation by a medical practitioner based on Common Terminology Criteria for Adverse Event Version 4.0, JCOG Japanese translation (henceforth also abbreviated as NCI-CTCAE), and evaluation by a patient based on Functional Assessment of Cancer Therapy/Gynecologic Oncology Group-Neurotoxicity (Version 4) (henceforth also abbreviated as FACT/GOG-NTX-12).

According to NCI-CTCAE, a medical practitioner can confirm effects on motor peripheral neuropathy or sensory peripheral neuropathy, and according to FACT/GOG-NTX-12, a patient can confirm effects on oxaliplatin-induced peripheral neuropathy. According to NCI-CTCAE, motor peripheral neuropathy or sensory peripheral neuropathy can be evaluated in 6 grades, i.e., no neuropathy, grade 1 (no symptom), grade 2 (moderate symptoms), grade 3 (severe symptoms), grade 4 (life-threatening symptoms), and grade 5 (death). According to FACT/GOG-NTX-12, a patient gives evaluation scores for evaluation items (12 items) selected from 0 (not applied at all), 1 (slightly applied), 2 (somewhat applied), 3 (considerably applied), and 4 (applied very much), and degree of the effect can be evaluated with the evaluation scores (=48−Evaluation score given by patient), of which higher number means higher effect.

For one embodiment, although the human cancer patient is not particularly limited so long as the patient is a human cancer patient for whom a treatment with oxaliplatin is needed, human cancer patients suffering from large bowel cancer, pancreatic cancer, or gastric cancer can be exemplified. For another embodiment, human cancer patients suffering from large bowel cancer or gastric cancer can be exemplified. For another embodiment, human cancer patients suffering from large bowel cancer can be exemplified. Examples of the large bowel cancer include rectal cancer and colon cancer.

For one embodiment, thrombomodulin can be also used in an adjuvant chemotherapy aiming at suppression of postoperative recurrence. It can also be administered to a human cancer patient with recurrent cancer or metastatic cancer.

According to one embodiment, the cycle of the treatment with an anti-malignant tumor agent is one unit of a treatment with the anti-malignant tumor agent consisting of a combination of a treatment with the anti-malignant tumor agent for a certain period and withdrawal of the agent for a certain period. The day on which administration of the anti-malignant tumor agent (oxaliplatin) is started is defined as the first day of one cycle.

According to one embodiment, examples of the treatment with an anti-malignant tumor agent consisting of repetition of a single cycle comprising intravenous administration of oxaliplatin to a human cancer patient and following drug withdrawal include a treatment consisting of repetition of a single cycle comprising 1 to 6 times of intravenous administration of oxaliplatin to a human cancer patient and following drug withdrawal for at least 6 days. Oxaliplatin can be used, for example, according to the instructions described on the package insert of ELPLAT (registered trademark) or the label of Eloxatin.

As the number of times of the administration of oxaliplatin in 1 cycle of the anti-malignant tumor treatment with oxaliplatin, 1 to 6 times can be exemplified, 1 to 3 times can be exemplified for another embodiment, and 1 time can be exemplified for still another embodiment. When the anti-malignant tumor agent is administered twice or more in 1 cycle, one time of administration in two weeks can be exemplified, one time of administration in one week can be exemplified for another embodiment, and every day administration can be exemplified for still another embodiment. The anti-malignant tumor agent is administered once a day.

As the period of the drug withdrawal of the anti-malignant tumor agent (oxaliplatin) in one cycle of the anti-malignant tumor treatment with oxaliplatin, at least 6 days can be exemplified, at least 13 days can be exemplified for another embodiment, and at least 20 days can be exemplified for still another embodiment. Further, 6 to 24 days can be exemplified for still another embodiment, 13 to 24 days can be exemplified for still another embodiment, and 13 to 20 days can be exemplified for still another embodiment. Examples further include 13 days for still another embodiment, and 20 days for still another embodiment. When severe side reactions are induced by administration of oxaliplatin, the drug withdrawal of oxaliplatin of 3 to 6 weeks may be used for a certain period of time, and such a configuration also constitutes one embodiment.

As the number of times of the repetition of the single cycle in the anti-malignant tumor treatment with oxaliplatin, 1 to 24 times can be exemplified, 1 to 18 times can be exemplified for another embodiment, and 1 to 12 times can be exemplified for still another embodiment. Examples further include 1 to 6 times for still another embodiment. Examples still further include at least 6 times for still another embodiment. Examples still further include at least 8 times for still another embodiment. Examples still further include at least 12 times for still another embodiment. Examples still further include at least 18 times for still another embodiment. Examples still further include at least 24 times for still another embodiment.

As the dose of oxaliplatin per single administration include 50 to 150 mg/m$^2$ of body surface area of human cancer patient can be exemplified, 80 to 140 mg/m$^2$ can be exemplified for another embodiment, and 80 to 90 mg/m$^2$ can be exemplified for still another embodiment. Examples further include 90 to 110 mg/m$^2$ for still another embodiment, 120 to 140 mg/m$^2$ for still another embodiment, 85 mg/m$^2$ for still another embodiment, 100 mg/m$^2$ for still another embodiment, and 130 mg/m$^2$ for still another embodiment.

Body surface area of a human cancer patient can be obtained from body height and weight of the human cancer patient. The body surface area can be appropriately calculated according to common technical knowledge, and it can be calculated, for example, in accordance with the following DuBois' equation (Dubois D. and Dubois E. F.: Arch. Intern. Med., 17, 863-871, 1916).

$$\text{Body surface area } (m^2) = [\text{Body height } (cm)]^{0.725} \times [\text{Body weight } (kg)]^{0.425} \times 0.007184$$

Although intravenous administration rate of oxaliplatin is not particularly limited so long as it is the usual drip infusion rate, it is, for example, such a rate that required amount of oxaliplatin is administered within 3 hours, or such a rate that required amount of oxaliplatin is administered within 2 hours for another embodiment.

Examples of the anti-malignant tumor treatment with oxaliplatin include the following (a) to (f).
(a) A single cycle consisting of intravenous administration of 80 to 90 mg/m$^2$ (body surface area) of oxaliplatin once a day to a human cancer patient and drug withdrawal for at least 13 days is repeated.
(b) A single cycle consisting of intravenous administration of 85 mg/m$^2$ (body surface area) of oxaliplatin once a day to a human cancer patient and drug withdrawal for at least 13 days is repeated.

(c) A single cycle consisting of intravenous administration of 90 to 110 mg/m² (body surface area) of oxaliplatin once a day to a human cancer patient and drug withdrawal for at least 13 days is repeated.
(d) A single cycle consisting of intravenous administration of 100 mg/m² (body surface area) of oxaliplatin once a day to a human cancer patient and drug withdrawal for at least 20 days is repeated.
(e) A single cycle consisting of intravenous administration of 120 to 140 mg/m² (body surface area) of oxaliplatin once a day to a human cancer patient and drug withdrawal for at least 20 days is repeated.
(f) A single cycle consisting of intravenous administration of 130 mg/m² (body surface area) of oxaliplatin once a day to a human cancer patient and drug withdrawal for at least 20 days is repeated.

According to one embodiment, oxaliplatin can be administered in combination with one or several kinds of anti-malignant tumor agents of different action mechanisms. For example, oxaliplatin can be administered by the FOLFOX therapy. The FOLFOX therapy is one class of anti-malignant tumor chemotherapy that uses oxaliplatin in combination with fluorouracil, and levofolinate. The FOLFOX therapy is classified into, for example, FOLFOX2, FOLFOX3, FOLFOX4, FOLFOX6, mFOLFOX6, FOLFOX7, mFOLFOX7, and the like according to the administration method. Oxaliplatin can also be administered by the XELOX therapy (CapeOX therapy), FOLFOXIRI therapy, FOLFIRINOX therapy, or SOX therapy. The XELOX therapy is an anti-malignant tumor treatment that uses oxaliplatin in combination with capecitabine. The FOLFOXIRI therapy or FOLFIRINOX therapy is an anti-malignant tumor treatment that uses oxaliplatin in combination with irinotecan hydrochloride hydrate, fluorouracil, and levofolinate. The SOX therapy is an anti-malignant tumor treatment that uses oxaliplatin in combination with S-1 (combined formulation of tegafur, gimeracil, and oteracil potassium).

Examples of the anti-malignant tumor agent to be administered in combination with oxaliplatin include fluorouracil, capecitabine, tegafur gimeracil-oteracil potassium formulation, irinotecan, bevacizumab, cetuximab, panitumumab, and trastuzumab.

According to one embodiment, oxaliplatin can be administered in combination with an antiemetic agent or an antiallergic agent.

According to one embodiment, thrombomodulin can be intravenously administered on the first day of each cycle of the anti-malignant tumor agent treatment. Thrombomodulin can be administered once in one cycle.

According to one embodiment, thrombomodulin can be administered before the start of the administration of the anti-malignant tumor agent. It can also be administered after the start of the administration of the anti-malignant tumor agent. It is also possible to simultaneously start the administrations of thrombomodulin and the anti-malignant tumor agent.

When thrombomodulin is administered before the start of the administration of the anti-malignant tumor agent, the period of from the administration of thrombomodulin to the start of the administration of the anti-malignant tumor agent is not particularly limited so long as the effects of the anti-malignant tumor agent for mitigating conditions and/or suppressing onset of a peripheral neuropathy can be exhibited. However, thrombomodulin can be administered, for example, 9 days before the start of the administration of the anti-malignant tumor agent or thereafter, 7 days before the start of the administration of the anti-malignant tumor agent or thereafter according to another embodiment, 5 days before the start of the administration of the anti-malignant tumor agent or thereafter according to still another embodiment, 3 days before the start of the administration of the anti-malignant tumor agent or thereafter according to still another embodiment, 1 day before the start of the administration of the anti-malignant tumor agent or thereafter according to still another embodiment, or 12 hours before the start of the administration of the anti-malignant tumor agent or thereafter according to still another embodiment, When thrombomodulin is administered after the start of the administration of the anti-malignant tumor agent, the period of from the start of the administration of the anti-malignant tumor agent to the administration of thrombomodulin is not particularly limited so long as the effects of the anti-malignant tumor agent for mitigating conditions and/or suppressing onset of a peripheral neuropathy can be exhibited. However, thrombomodulin can be administered, for example, 8 days after the start of the administration of the anti-malignant tumor agent or earlier, 6 days after the start of the administration of the anti-malignant tumor agent or earlier according to another embodiment, 4 days after the start of the administration of the anti-malignant tumor agent or earlier according to still another embodiment, 2 days after the start of the administration of the anti-malignant tumor agent or earlier according to still another embodiment, 6 hours after the start of the administration of the anti-malignant tumor agent or earlier according to still another embodiment, or 1 hour after the start of the administration of the anti-malignant tumor agent or earlier according to still another embodiment.

In one embodiment, the medicament of the present invention can contain a carrier. As the carrier usable in the present invention, a water-soluble carrier is preferred, and for example, the medicament of the present invention can be prepared by adding sucrose, glycerin, pH modifier consisting of an inorganic salt, or the like as additives. Further, if necessary, amino acids, salts, carbohydrates, surfactants, albumin, gelatin or the like may be added as disclosed in Japanese Patent Unexamined Publication (KOKAI) Nos. 1-6219 and 6-321805, and it is also preferable to add a preservative. Preferred examples of preservative include parabenzoic acid esters, and a particularly preferred example is methyl parabenzoate. Amount of preservative to be added is usually 0.01 to 1.0% (in terms of weight %, the same shall apply to the following descriptions), preferably 0.1 to 0.3%. Method for adding these additives is not particularly limited. In the case of preparing a lyophilized product, examples of the method include, for example, a method of mixing a solution containing an anti-malignant tumor agent and a solution containing thrombomodulin, and then adding additives to the mixture, and a method of mixing additives with an anti-malignant tumor agent dissolved in water, water for injection, or an appropriate buffer beforehand, adding a solution containing thrombomodulin to the mixture, mixing the resulting mixture to prepare a solution, and lyophilizing the solution, in such manners as those commonly employed. As an embodiment, the medicament of the present invention may be provided in the form of an injection, or in the form of a lyophilized preparation to be dissolved upon use.

Examples of the preparation method of the medicament include a method of filling a solution containing 0.05 to 15 mg/mL, preferably 0.1 to 5 mg/mL, of thrombomodulin, and the aforementioned additives in water, water for injection, or an appropriate buffer in an ampoule or vial in a volume of, for example, 0.5 to 10 mL, freezing the solution, and drying the solution under reduced pressure. Such a solution, per se, can be prepared as an aqueous solution preparation for injection.

Although the administration method of the medicament of the present invention is not particularly limited so long as the effects of the anti-malignant tumor agent for mitigating conditions and/or suppressing onset of a peripheral neuropathy can be exhibited, for one embodiment, intravenous administration can be exemplified.

Examples of method for the intravenous administration include a method of administering a desired dose of the medicament at one time, and intravenous administration by drip infusion.

The method of administering a desired dose of the medicament at one time (intravenous bolus administration) is preferred from the viewpoint that the method requires only a short time for administration. When the medicament is administered at one time, a period required for administration by using an injectable syringe may generally varies. In general, the period of time required for the administration is, for example, 5 minutes or shorter, preferably 3 minutes or shorter, more preferably 2 minutes or shorter, still more preferably 1 minute or shorter, particularly preferably 30 seconds or shorter, although it depends on a volume to be administered. Although the minimum administration time is not particularly limited, the period is preferably 1 second or longer, more preferably 5 seconds or longer, still more preferably 10 seconds or longer. The dose is not particularly limited so long as the dose is within the aforementioned preferred range of the dose. Intravenous administration by drip infusion is also preferred from a viewpoint that blood level of thrombomodulin can be easily kept constant.

For one embodiment, the daily dose of thrombomodulin is, for example, 0.06 mg/kg, although it may vary depending on age, body weight of patients, severity of disease, administration route and the like.

As described in the drawing included in the package insert of Recomodulin (registered trademark), "Pharmacokinetics", 1. (2), 0.06 mg/kg of Thrombomodulin alfa (genetical recombination) corresponds to 380 U/kg. That is, "0.06 mg/kg" of thrombomodulin may be read as "380 U/kg".

In one embodiment, the medicament of the present invention exhibits the effects of the mitigating conditions of and/or suppressing onset of a peripheral neuropathy induced by an anti-malignant tumor agent. To mitigate conditions means to reduce severity of conditions that are usually produced when oxaliplatin is administered, for example, sensory paralysis, pricking pain, and discomfort of extremities, as well as pain of extremities felt at exposure to low temperature. To suppress onset means to suppress level of a peripheral neuropathy that is usually produced when oxaliplatin is administered, for example, motor peripheral neuropathy and sensory peripheral neuropathy, to be a certain level or lower (for example, grade 1 or lower according to NCI-CTCAE). Pains of extremities can be evaluated according to Numerical Rating Scale (henceforth it may be abbreviated as NRS). According to NRS, strength of pain can be evaluated in 11 stages from stage 0, which means completely no pain, to stage 10, which means the expectable strongest pain.

According to one embodiment, when the anti-malignant tumor treatment with oxaliplatin is performed with one or more cycles, the medicament of the present invention can suppress reduction of total dose of oxaliplatin to be eventually administered compared with the total dose (A) that means the total of the doses of oxaliplatin of all the cycles to be usually administered to a human cancer patient. The degree of suppressing reduction of the total dose of oxaliplatin is not particularly limited so long as the difference between A and the total dose of oxaliplatin to be administered in one or more cycles of the anti-malignant tumor treatment with oxaliplatin using administration of the medicament of the present invention (B) is smaller than the difference between A and the total dose of oxaliplatin to be administered in one or more cycles of the anti-malignant tumor treatment with oxaliplatin without using administration of the medicament of the present invention (C). As for the suppression of reduction of the total dose of oxaliplatin, the ratio of B to A as average total doses is, for example, at least 70%, at least 80% for another embodiment, at least 85% for still another embodiment, at least 90% for still another embodiment, or at least 95% for still another embodiment. As for the suppression of reduction of the total dose of oxaliplatin, the ratio of B to C as average total doses is, for example, at least 101%, at least 102% for another embodiment, at least 103% for still another embodiment, at least 104% for still another embodiment, at least 105% for still another embodiment, at least 110% for still another embodiment, at least 115% for still another embodiment, or at least 120% for still another embodiment.

According to one embodiment, the medicament of the present invention can be used as a safe medicament providing less side reactions.

According to one embodiment, the medicament of the present invention can be administered together with one or more kinds of other medicaments used for treating peripheral neuropathies caused by anti-malignant tumor agents, for example, one or two or more kinds of medicaments selected from Chinese orthodox medicines, steroids, antidepressants, antiepileptics, opioids, and the like, or can be prepared as a mixture with such one or two or more kinds of medicaments as mentioned above, and administered. Further, thrombomodulin may be administered with performing physiotherapy, complementary therapies such as massage and acupuncture, and the like.

EXAMPLES

Hereafter, the present invention will be explained in more detail with reference to examples of the present invention, comparative example, and preparation examples. However, the present invention is not limited by these examples at all.
[Explanation of Sequence Listing]
SEQ ID NO: 1: Amino acid sequence encoded by the gene used in production of ART-123
SEQ ID NO: 2: Nucleotide sequence encoding the amino acid sequence of SEQ ID NO: 1
SEQ ID NO: 3: Amino acid sequence encoded by the gene used in production of ART-123M
SEQ ID NO: 4: Nucleotide sequence encoding the amino acid sequence of SEQ ID NO: 3
SEQ ID NO: 5: Synthetic DNA for mutation used for carrying out site-directed mutagenesis The thrombomodulin for the present invention used in the examples and comparative examples was prepared according to the aforementioned method of Yamamoto et al. (the method described in Japanese Patent Unexamined Publication (KOKAI) No. 64-6219). Preparation examples thereof are described below. Safety of the thrombomodulins obtained in these preparation examples was confirmed by single and repetitive intravenous administration tests using rats and monkeys, mouse reproduction test, local irritation test, pharmacological safety test, virus inactivation test, and the like.

Preparation Example 1

<Obtaining Thrombomodulin>

A highly purified product was obtained by the aforementioned method. Specifically, Chinese hamster ovary (CHO) cells were transfected with a DNA encoding the amino acid sequence of SEQ ID NO: 1 (which specifically consisted of the nucleotide sequence of SEQ ID NO: 2). From the culture of the above transformant cells, a highly purified product was obtained by collecting an active fraction with a 20 mmol/L phosphate buffer (pH 7.3) containing 50 mmol/L NaCl according to the aforementioned conventional purification method. The product was further concentrated by ultrafiltration to obtain a thrombomodulin (ART-123) solution having a concentration of 11.2 mg/mL.

<Preparation of Additive Solution>

Arginine hydrochloride (480 g, Ajinomoto) was weighed, put into a 10-L volume stainless steel vessel, added with water for injection (5 L), and dissolved. The solution was adjusted to pH 7.3 by adding a 1 mol/L sodium hydroxide solution.

<Preparation and Filling of Drug Solution>

The total volume of the additive solution obtained above was put into a 20-L stainless steel vessel, and added with the ART-123 solution obtained above (2398 mL, corresponding to 26.88 g of soluble thrombomodulin protein, added in a 12% excess amount), and the mixture was stirred. The mixture was further added with water for injection to obtain a total volume of 12 L, and the mixture was made uniform by stirring. This drug solution was subjected to filtration sterilization using a filter having a pore diameter of 0.22 μm (MCGL10S, manufactured by Millipore). The filtrate was filled in vials in a volume of 1 mL each, and the vials were half-closed with rubber stoppers.

<Lyophilization>

A lyophilization step was performed under the following conditions in the order of lyophilization→filling nitrogen-→complete closing with rubber stopper→screwing cap to obtain a ART-123-containing preparation containing 2 mg of soluble thrombomodulin and 40 mg of arginine hydrochloride in one vial.

<Lyophilization Conditions>

Preliminary cooling (from room temperature to 15° C. over 15 minutes)→main cooling (from 15° C. to −45° C. over 2 hours)→retention (−45° C. for 2 hours)→start of vacuuming (−45° C. for 18 hours)→temperature increase (from −45° C. to 25° C. over 20 hours)→retention (25° C. for 15 hours)→temperature increase (from 25° C. to 45° C. over 1 hour)→retention (45° C. for 5 hours)→room temperature (from 45° C. to 25° C. over 2 hours)→pressure recovery and nitrogen filling (up to −100 mmHg)→complete closure with stopper→screwing cap Preparation Example 2

Chinese hamster ovary (CHO) cells are transfected with a DNA encoding the amino acid sequence of SEQ ID NO: 3 (which specifically consists of the nucleotide sequence of SEQ ID NO: 4), a solution of thrombomodulin purified from a culture of the above transformant cells (henceforth also abbreviated as ART-123M in the specification) by the aforementioned conventional purification method is obtained, and a lyophilized ART-123M preparation is obtained in the same manner as that described above.

Example 1

Effect of Single Administration of ART-123 in One Cycle on Oxaliplatin-Induced Peripheral Neuropathy in Human Cancer Patient <Test Method>

A placebo controlled test was performed in order to examine effectiveness of ART-123 on onset of oxaliplatin-induced peripheral neuropathy at the time of performing postoperative adjuvant chemotherapy using oxaliplatin in colon cancer patients of pathological stage II or III after radical cure operation (R0 operation), and safety of the same.

The postoperative adjuvant chemotherapy using oxaliplatin was performed according to the mFOLFOX6 method (administration is repeated by repetition of a single cycle consisting of intravenous administration of 85 mg/m$^2$ (body surface area) of oxaliplatin by drip infusion once a day over 2 hours, and drug withdrawal for at least 13 days), and the cycle was repeated 12 times. The test subjects were randomly divided into three groups, placebo group, single ART-123 administration group, and triple ART-123 administration group. In the placebo group, a placebo was administered on the first, second and third days of each cycle. In the single ART-123 administration group, 0.06 mg/kg of ART-123 was administered on the first day of each cycle, and the placebo was administered on the second and third days of each cycle. In the triple ART-123 administration group, 0.06 mg/kg of ART-123 was administered on the first, second and third days of each cycle. On the first day, the administration of ART-123 as the trial drug or the placebo by intravenous administration by drip infusion was started 2 hours to 30 minutes before the administration of oxaliplatin, continued over 30 minutes, and ended before the start of the oxaliplatin administration. On the second and third days, the administration of ART-123 or the placebo was started in the same time zone as that of the first day as much as possible, and intravenous administration by drip infusion was carried out over 30 minutes.

During the administration period, combined use of other trial drugs, Recomodulin (registered trademark), anti-malignant tumor agents other than the drug used in the postoperative adjuvant chemotherapy specified in this trial, and thrombolytic agents (t-PA preparation, urokinase, etc.) was inhibited. Further, except for a period during which motor peripheral neuropathy or sensory peripheral neuropathy is evaluated to be at grade 2 or higher grade by a medical practitioner responsible for the trial or a medical practitioner assigned the trial according to Common Terminology Criteria for Adverse Event Version 4.0, JCOG Japanese translation (henceforth abbreviated as NCI-CTCAE), combined use of drugs considered to affect peripheral neuropathies was inhibited.

For the evaluation of peripheral neuropathies by patients, Functional Assessment of Cancer Therapy/Gynecologic Oncology Group-Neurotoxicity (Version 4) (henceforth abbreviated as FACT/GOG-NTX-12), and NRS (pain) were used, and for the evaluation by medical practitioners, criteria of motor peripheral neuropathy and sensory peripheral neuropathy defined in NCI-CTCAE were used.

<Results>
1. Effect for Mitigating Conditions of Peripheral Neuropathy

Changes of the least square averages evaluated from the start of the administration of the trial drug to the completion of the trial according to FACT/GOG-NTX-12 for the groups, and differences thereof between the placebo group and the single ART-123 administration group or triple ART-123 administration group are shown in Table 1. Values obtained by subtracting evaluation scores given by patients from 48 were used as evaluation scores. The scores obtained after 12 cycles for both the ART-123 administration groups were higher than that of the placebo group, and thus ART-123 reduced the conditions of peripheral neuropathies. Further, the single ART-123 administration group showed higher effect for mitigating conditions of peripheral neuropathies compared with the triple ART-123 administration group.

When pains of extremities were evaluated according to NRS, the analgesic effect observed in the single ART-123 administration group was higher than that observed in the triple ART-123 administration group.

TABLE 1

State of peripheral neuropathies evaluated by patients

FACT/GOG-NTX-12

| | | | | Difference in least square average | |
| --- | --- | --- | --- | --- | --- |
| | Placebo group (N = 28) Least square average (standard error) [95% confidence interval] | Single ART-123 administration group (N = 27) Least square average (standard error) [95% confidence interval] | Triple ART-123 administration group (N = 24) Least square average (standard error) [95% confidence interval] | Single ART-123 administration group vs Placebo group Least square average (standard error) [95% confidence interval] | Triple ART-123 administration group vs Placebo group Least square average (standard error) [95% confidence interval] |
| Base line | 46.4 (0.4) [45.5, 47.3] | 46.7 (0.5) [45.8, 47.6] | 46.3 (0.5) [45.4, 47.3] | 0.3 (0.6) [−1.0, 1.6] | −0.1 (0.7) [−1.4, 1.3] |
| Cycle 1 | 42.3 (0.9) [40.5, 44.0] | 43.0 (0.9) [41.2, 44.8] | 43.9 (1.0) [42.0, 45.8] | 0.8 (1.3) [−1.8, 3.3] | 1.6 (1.3) [−1.0, 4.2] |
| Cycle 2 | 38.0 (1.4) [35.2, 40.9] | 41.9 (1.5) [39.0, 44.7] | 41.7 (1.5) [38.6, 44.7] | 3.8 (2.0) [−0.3, 7.9] | 3.6 (2.1) [−0.6, 7.8] |
| Cycle 3 | 36.2 (1.5) [33.2, 39.2] | 40.0 (1.5) [36.9, 43.0] | 40.6 (1.6) [37.4, 43.9] | 3.8 (2.2) [−0.5, 8.1] | 4.4 (2.2) [0.0, 8.8] |
| Cycle 4 | 34.6 (1.7) [31.2, 38.0] | 38.7 (1.7) [35.3, 42.1] | 40.2 (1.8) [36.5, 43.8] | 4.2 (2.4) [−0.6, 9.0] | 5.6 (2.5) [0.6, 10.6] |
| Cycle 5 | 33.9 (1.8) [30.3, 37.5] | 37.9 (1.8) [34.3, 41.5] | 39.2 (1.9) [35.4, 43.0] | 4.0 (2.5) [−1.0, 9.0] | 5.3 (2.6) [0.1, 10.5] |
| Cycle 6 | 36.1 (1.5) [33.1, 39.1] | 39.1 (1.5) [36.1, 42.1] | 38.3 (1.6) [35.1, 41.5] | 3.0 (2.1) [−1.3, 7.2] | 2.2 (2.2) [−2.2, 6.6] |
| Cycle 7 | 34.5 (1.6) [31.4, 37.6] | 38.6 (1.6) [35.5, 41.7] | 38.3 (1.6) [35.0, 41.6] | 4.1 (2.2) [−0.3, 8.5] | 3.8 (2.3) [−0.7, 8.3] |
| Cycle 8 | 34.1 (1.8) [30.6, 37.6] | 37.6 (1.8) [34.1, 41.1] | 37.7 (1.9) [34.0, 41.4] | 3.5 (2.5) [−1.4, 8.5] | 3.6 (2.6) [−1.5, 8.7] |
| Cycle 9 | 31.9 (1.8) [28.2, 35.5] | 36.9 (1.8) [33.3, 40.6] | 36.8 (1.9) [33.0, 40.6] | 5.1 (2.6) [−0.1, 10.2] | 4.9 (2.6) [−0.4, 10.2] |
| Cycle 10 | 31.1 (1.8) [27.5, 34.7] | 36.7 (1.8) [33.1, 40.3] | 36.6 (1.9) [32.8, 40.4] | 5.6 (2.6) [0.5, 10.7] | 5.5 (2.6) [0.2, 10.7] |
| Cycle 11 | 29.1 (1.9) [25.3, 33.0] | 36.8 (1.9) [33.0, 40.7] | 33.3 (2.0) [29.3, 37.3] | 7.7 (2.7) [2.3, 13.2] | 4.2 (2.8) [−1.3, 9.7] |
| Cycle 12 | 28.9 (L9) [25.0, 32.8] | 36.3 (1.9) [32.4, 40.1] | 32.3 (2.0) [28.4, 36.3] | 7.3 (2.7) [1.9, 12.8] | 3.4 (2.8) [−2.1, 9.0] |
| After cycle 12 | 30.4 (2.1) [26.3, 34.5] | 35.4 (2.0) [31.3, 39.5] | 34.1 (2.1) [29.9, 38.4] | 5.0 (2.9) [−0.8, 10.8] | 3.7 (3.0) [−2.2, 9.6] |

2. Effect for Suppressing Onset of Peripheral Neuropathy (Sensory Peripheral Neuropathy)

Cumulative grade 2 or higher grade observation ratios (ratios of cases that showed the neuropathy of the grade 2 or higher grade at least once up to each cycle) of the administration groups evaluated according to NCI-CTCAE (sensory peripheral neuropathy) in the period of from the start of the administration of the trial drug to the completion of the trial, and differences thereof between the placebo group and the single ART-123 administration group or triple administration group are shown in Table 2. At the time of the cycle 12, both the cumulative grade 2 or higher grade observation ratios of the ART-123 administration groups were lower than that of the placebo group, and thus ART-123 suppressed onset of the peripheral neuropathy. Further, higher peripheral neuropathy onset-suppressing effect was observed for the single ART-123 administration group compared with the triple ART-123 administration group.

TABLE 2

State of peripheral neuropathy (sensory peripheral neuropathy) evaluated by medical practitioners NCI-CTCAE (sensory peripheral neuropathy)

| | Placebo group (N = 28) | | Single ART-123 administration group (N = 27) | | | | Triple ART-123 administration group (N = 24) | | | |
| --- | --- | --- | --- | --- | --- | --- | --- | --- | --- | --- |
| | | | | Cumulative ratio of grade 2 or higher grade | | | | Cumulative ratio of grade 2 or higher grade | | |
| | No symptom or grade 1 n (%) | Cumulative ratio of grade 2 or higher grade n (%) | No symptom or grade 1 n (%) | n (%) | Difference with respect to placebo group [95% confidence interval] | P value | No symptom or grade 1 n (%) | n (%) | Difference with respect to placebo group [95% confidence interval] | P value |
| Base line | 28 (100.0) | 0 (0.0) | 27 (100.0) | 0 (0.0) | — | — | 24 (100.0) | 0 (0.0) | — | — |
| Cycle 1 | 27 (96.4) | 1 (3.6) | 27 (100.0) | 0 (0.0) | −3.6 (−29.4, 22.5) | 1.0000 | 24 (100.0) | 0 (0.0) | −3.6 (−30.6, 23.9) | 1.0000 |
| Cycle 2 | 26 (92.9) | 2 (7.1) | 27 (100.0) | 0 (0.0) | −7.1 (−32.8, 19.0) | 0.4909 | 24 (100.0) | 0 (0.0) | −7.1 (−33.9, 20.4) | 0.4932 |
| Cycle 3 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 4 | 23 (82.1) | 5 (17.9) | 23 (85.2) | 4 (14.8) | −3.0 (−29.4, 22.5) | 1.0000 | 22 (91.7) | 2 (8.3) | −9.5 (−35.9, 17.8) | 0.4300 |
| Cycle 5 | 22 (78.6) | 6 (21.4) | 22 (81.5) | 5 (18.5) | −2.9 (−29.4, 22.5) | 1.0000 | 22 (91.7) | 2 (8.3) | −13.1 (−39.2, 14.2) | 0.2615 |
| Cycle 6 | 21 (75.0) | 7 (25.0) | 22 (81.5) | 5 (18.5) | −6.5 (−32.8, 19.0) | 0.7458 | 21 (87.5) | 3 (12.5) | −12.5 (−38.8, 15.0) | 0.3087 |
| Cycle 7 | 17 (60.7) | 11 (39.3) | 22 (81.5) | 5 (18.5) | −20.8 (−46.0, 4.6) | 0.1379 | 20 (83.3) | 4 (16.7) | −22.6 (−47.9, 5.2) | 0.1238 |
| Cycle 8 | 16 (57.1) | 12 (42.9) | 21 (77.8) | 6 (22.2) | −20.6 (−46.0, 4.6) | 0.1516 | 19 (79.2) | 5 (20.8) | −22.0 (−47.3, 5.8) | 0.1389 |
| Cycle 9 | 15 (53.6) | 13 (46.4) | 18 (66.7) | 9 (33.3) | −13.1 (−39.3, 13.4) | 0.4121 | 18 (75.0) | 6 (25.0) | −21.4 (−46.6, 6.2) | 0.1516 |
| Cycle 10 | 11 (39.3) | 17 (60.7) | 16 (59.3) | 11 (40.7) | −20.0 (−45.3, 7.5) | 0.1810 | 16 (66.7) | 8 (33.3) | −27.4 (52.1, 0.3) | 0.0581 |
| Cycle 11 | 11 (39.3) | 17 (60.7) | 16 (59.3) | 11 (40.7) | −20.0 (−45.3, 7.5) | 0.1810 | 13 (54.2) | 11 (45.8) | −14.9 (−41.0, 12.9) | 0.4033 |
| Cycle 12 | 10 (35.7) | 18 (64.3) | 16 (59.3) | 11 (40.7) | −23.5 (−48.4, 4.0) | 0.1078 | 13 (54.2) | 11 (45.8) | −18.5 (−44.2, 9.4) | 0.2635 |
| After cycle 12 | 10 (35.7) | 18 (64.3) | 15 (55.6) | 12 (44.4) | −19.8 (−45.0, 7.8) | 0.1799 | 11 (45.8) | 13 (54.2) | −10.1 (−36.4, 17.4) | 0.5735 |

3. Effect for Suppressing Onset of Peripheral Neuropathy (Motor Peripheral Neuropathy)

Cumulative grade 2 or higher grade observation ratios (ratios of cases that showed the neuropathy of the grade 2 or higher grade at least once up to each cycle) of the administration groups evaluated according to NCI-CTCAE (motor peripheral neuropathy) in the period of from the start of the administration of the trial drug to the completion of the trial, and differences thereof between the placebo group and the single ART-123 administration group or triple administration group are shown in Table 3. At the time of the cycle 12, the cumulative grade 2 or higher grade observation ratios of both the ART-123 administration groups were lower than that of the placebo group, and thus ART-123 suppressed onset of the peripheral neuropathy. Further, higher peripheral neuropathy onset-suppressing effect was observed for the single ART-123 administration group compared with the triple ART-123 administration group.

TABLE 3

State of peripheral neuropathy (motor peripheral neuropathy) evaluated by medical practitioners NCI-CTCAE (motor peripheral neuropathy)

| | Placebo group (N = 28) | | Single ART-123 administration group (N = 27) | | | | Triple ART-123 administration group (N = 24) | | | |
|---|---|---|---|---|---|---|---|---|---|---|
| | | | | Cumulative ratio of grade 2 or higher grade | | | | Cumulative ratio of grade 2 or higher grade | | |
| | No symptom or grade 1 n (%) | Cumulative ratio of grade 2 or higher grade n (%) | No symptom or grade 1 n (%) | n (%) | Difference with respect to placebo group [95% confidence interval] | P value | No symptom or grade 1 n (%) | n (%) | Difference with respect to placebo group [95% confidence interval] | P value |
| Base line | 28 (100.0) | 0 (0.0) | 27 (100.0) | 0 (0.0) | — | — | 24 (100.0) | 0 (0.0) | — | — |
| Cycle 1 | 27 (96.4) | 1 (3.6) | 27 (100.0) | 0 (0.0) | −3.6 (−29.4, 22.5) | 1.0000 | 24 (100.0) | 0 (0.0) | −3.6 (−30.6, 23.9) | 1.0000 |
| Cycle 2 | 26 (92.9) | 2 (7.1) | 27 (100.0) | 0 (0.0) | −7.1 (−32.8, 19.0) | 0.4909 | 24 (100.0) | 0 (0.0) | −7.1 (−33.9, 20.4) | 0.4932 |
| Cycle 3 | 26 (92.9) | 2 (7.1) | 27 (100.0) | 0 (0.0) | −7.1 (−32.8, 19.0) | 0.4909 | 24 (100.0) | 0 (0.0) | −7.1 (−33.9, 20.4) | 0.4932 |
| Cycle 4 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 5 | 25 (89.3) | 3 (10.7) | 27 (100.0) | 0 (0.0) | −10.7 (−36.1, 15.4) | 0.2364 | 23 (95.8) | 1(4.2) | −6.5 (−33.2, 20.9) | 0.6146 |
| Cycle 6 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 7 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 8 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 9 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 10 | 25 (89.3) | 3 (10.7) | 27 (100.0) | 0 (0.0) | −10.7 (−36.1, 15.4) | 0.2364 | 23 (95.8) | 1 (4.2) | −6.5 (−33.2, 20.9) | 0.6146 |
| Cycle 11 | 23 (82.1) | 5 (17.9) | 27 (100.0) | 0 (0.0) | −17.9 (−42.7, 8.2) | 0.0515 | 23 (95.8) | 1 (4.2) | −13.7 (−39.6, 13.9) | 0.1994 |
| Cycle 12 | 22 (78.6) | 6 (21.4) | 27 (100.0) | 0 (0.0) | −21.4 (−46.0, 4.6) | 0.0232 | 23 (95.8) | 1 (4.2) | −17.3 (−42.9, 10.3) | 0.1072 |
| After cycle 12 | 21 (75.0) | 7 (25.0) | 26 (96.3) | 1 (3.7) | −21.3 (−46.0, 4.6) | 0.0511 | 22 (91.7) | 2 (8.3) | −16.7 (−42.5, 10.8) | 0.1525 |

4. Oxaliplatin Total Dose Reduction-Suppressing Effect

Cumulative doses as the oxaliplatin total doses from the start of the administration of the trial drug to the completion of the trial for the administration groups are shown in Table 4. The cumulative doses of the single ART-123 administration group and triple administration group were both higher than that of the placebo group for both the average value and median value.

TABLE 4

Cumulative oxaliplatin dose

| Cumulative oxaliplatin dose (mg/m$^2$) | Placebo group | Single ART-123 administration group | Triple ART-123 administration group |
|---|---|---|---|
| N | 28 | 27 | 24 |
| Average (standard deviation) | 719.89 (264.40) | 817.51 (182.58) | 850.90 (189.41) |
| Median | 819.07 | 849.24 | 920.68 |
| Minimum and maximum values | 83.7:999.7 | 331.2:1036.6 | 255.1:1012.3 |
| First guartile, third quartile | 578.18, 905.50 | 692.06, 952.81 | 787.00, 980.46 |

5. Safety

As for the adverse events observed in the period of from the start of the administration of the trial drug to the completion of the trial, numbers and ratios of the observed adverse events for the administration groups, and differences of the ratios between the placebo group and the single ART-123 administration group or triple administration group are shown in Table 5, which are categorized according to presence or absence of relation to the trial drug, severity, and relation to hemorrhage. Marked difference of ratios of the observed adverse events was not observed between the placebo group and both the single ART-123 administration group and triple administration group irrespective of the presence or absence of relation to the trial drug, severity, and relation to hemorrhage, and therefore it was confirmed that the drug can be safely administered.

TABLE 5

State of adverse events observed after administration of trial drug

|  | Placebo group (N = 28) n (%) | Single ART-123 administration group (N = 27) n (%) | Triple ART-123 administration group (N = 24) n (%) | Difference of ratios of observed adverse events between single ART-123 administration group and placebo group [95% confidence interval] | Difference of ratios of observed adverse events between triple ART-123 administration group and placebo group [95% confidence interval]) |
|---|---|---|---|---|---|
| Adverse events |  |  |  |  |  |
| Total adverse events | 28 (100.0) | 27 (100.0) | 24 (100.0) | — | — |
| Adverse events relating to trial drug | 0 (0.0) | 2 (7.4) | 3 (12.5) | 7.4 (−19.0, 32.8) | 12.5 (−15.0, 38.8) |
| Severe adverse events |  |  |  |  |  |
| Total severe adverse events | 2 (7.1) | 5 (18.5) | 3 (12.5) | 11.4 (−15.4, 36.1) | 5.4 (−21.7, 32.1) |
| Severe adverse events relating to trial drug | 0 (0.0) | 0 (0.0) | 0 (0.0) | — | — |
| Adverse events relating to hemorrhage |  |  |  |  |  |
| Total adverse events relating to hemorrhage | 2 (7.1) | 3 (11.1) | 6 (25.0) | 4.0 (−22.5, 29.4) | 17.9 (−9.9, 43.5) |
| Adverse events relating to hemorrhage | 0 (0.0) | 1 (3.7) | 2 (8.3) | 3.7 (−22.5, 29.4) | 8.3 (−19.2, 35.0) |

Comparative Example 1

Effect of Single ART-123 Administration in One Cycle on Oxaliplatin-Induced Peripheral Neuropathy in Animal Model In the case of peripheral neuropathies induced by an anti-malignant tumor agent, it is a problem that the conditions of the peripheral neuropathies are developed and aggravated by repetition of administration of the anti-malignant tumor agent, and it becomes difficult to continue the treatment with the anti-malignant tumor agent. It is important to continue the treatment with the anti-malignant tumor agent by mitigating conditions and/or suppressing onset of peripheral neuropathy induced by the treatment with the anti-malignant tumor agent. In order to examine number of times of administration of ART-123 in one cycle of oxaliplatin treatment concerning prophylactic effect of ART-123 for oxaliplatin-induced peripheral neuropathy, a rat oxaliplatin-induced peripheral neuropathy model evaluation system was constructed by single administration of the anti-malignant tumor agent. By using hyperalgesia (decrease of pressure pain threshold) developed in rat foot by single intraperitoneal administration of oxaliplatin as index of peripheral neuropathy, and administering ART-123 once a day from the day of the oxaliplatin administration, number of times of administration that can suppress onset of hyperalgesia over 14 days or 21 days, which corresponds to the period of one cycle of the treatment, was investigated.

1. Correlation of ART-123 Doses for Human and Rat Model

When ART-123 is intravenously administered to rats at a dose of 0.25 mg/kg, the pharmacokinetic parameters are as follows: initial plasma concentration ($C_0$) is 6.14 µg/mL, and half-life ($t_{1/2\beta}$) is 7.2 hours (New drug application summary of Recomodulin (registered trademark), paragraph 2.6.4.3.1.1). When ART-123 is intravenously administered to a human at a dose of 0.06 mg/kg, which is the clinical dose of ART-123, the highest plasma concentration of ART-123 is 0.9 to 1.7 µg/mL (New drug application summary of Recomodulin (registered trademark), paragraph 2.5.3.2.1), and the half-life is about 20 hours (New drug application summary of Recomodulin (registered trademark), paragraph 2.5.3.3). Since the half-lives in human and rat were significantly different as shown by comparison based on intravenous administration as described above, it was considered that it is difficult to attain change of plasma concentration close to that observed in human in rat by intravenous administration. Therefore, the pharmacokinetic parameters observed when the drag was intraperitoneally administered to rats were examined.

<Test Method>

ART-123 was intraperitoneally administered at a dose of 1 mg/kg to 7 to 8-weeks old Sprague Dawley male rats, and plasma was collected over time. Plasma concentration of the drug was measured by ELISA, and pharmacokinetic parameters were analyzed in a non-compartment model.

<Results>

When ART-123 was intraperitoneally administered at a dose of 1 mg/kg, the highest plasma concentration ($C_{max}$) was 5.47 µg/mL, time required to obtain the highest plasma concentration ($t_{max}$) was 6.00 hours, and half-life ($t_{1/2}$) was 14.1 hours as calculated from the change of the plasma concentration.

In consideration of the half-life of 14.1 hours and $t_{max}$ of 6 hours observed when ART-123 was intraperitoneally administered to rats at a dose of 1 mg/kg, it was considered that change of plasma concentration close to that observed in human by intravenous administration, in which the half-life is about 20 hours, can be attained in rats by intraperitoneal administration. Further, since $C_{max}$ of 5.47 μg/mL attained in rats by intraperitoneal administration of 1 mg/kg of ART-123 is about 3 to 6 times of the highest plasma concentration (0.9 to 1.7 μg/mL) obtainable in humans by intravenous administration of 0.06 mg/kg of ART-123, it was considered that intravenous administration of 0.06 mg/kg of ART-123 to a human substantially corresponds to intraperitoneal administration of about 0.15 to 0.3 mg/kg to a rat.

2. Effect of Administration of ART-123 Over 7 Days for Suppressing Onset of Oxaliplatin-Induced Peripheral Neuropathy in Rat Model <Test Method>

(1) Production of Oxaliplatin-Induced Peripheral Neuropathy Model Rat

The model was prepared by intraperitoneally administering oxaliplatin once at a dose of 6 mg/kg to 7-weeks old Sprague Dawley male rats as laboratory animals.

(2) Administration of Test Drug

To the rats administered with oxaliplatin, ART-123 was intraperitoneally administered 7 times in total at a frequency of once a day from the day of the oxaliplatin administration. The dose was 0.3 mg/kg, 1 mg/kg, or 10 mg/kg (the groups of these doses are referred to as 0.3 mg/kg, 1 mg/kg, and 10 mg/kg groups, respectively). The medium was also intraperitoneally administered once a day over 7 days as a negative control (medium group).

(3) Randall-Selitto Test

For the aforementioned rats, measurement was performed according to the foot pressure pain method (Randall-Selitto test) described in Randall L O. et al., Arch. Int. Pharmacodyn. Ther., 1957, 111, 409-419. That is, the right hind leg paw was gradually pressurized with a pressure pain analgesy meter, and the pressure observed when the animal showed an escape response was determined as the pressure pain escape threshold.

(4) Statistical Analysis

As for the action of ART-123, the pressure pain escape thresholds determined on the 14th and 21st days after the oxaliplatin administration were statistically analyzed. By using the medium group as a control, the parametric Williams test (ascending direction) was performed at a one-tailed significance level of 2.5% or less for the pressure pain escape thresholds observed in the 0.3 mg/kg, 1 mg/kg, and 10 mg/kg groups (*: $p<0.05$, and **: $p<0.01$ in FIG. 1). Further, a paired t-test was performed at a two-tailed significance level of 5% for the pressure pain escape thresholds of the medium group determined one day before the oxaliplatin administration and on the 14th or 21st day after the oxaliplatin administration (##: $p<0.01$ in FIG. 1).

<Results>

The results of the prophylactic administration of ART-123 to rats once a day for 7 days from the day of the oxaliplatin administration are shown in FIG. 1. In the control group, the pressure pain escape threshold was significantly lowered on the 14th and the 21st day after the oxaliplatin administration compared with that observed on the day before the day of the oxaliplatin administration, and thus hyperalgesia was developed. In the ART-123 administration groups, such fall of the pressure pain escape threshold as observed in the medium group was significantly suppressed from the dose of 0.3 mg/kg in a dose-dependent manner.

3. Effect for Suppressing Onset of Peripheral Neuropathy Induced by ART-123 Administration for 1 to 3 Days in Rat Model <Test Method>

(1) Preparation of Oxaliplatin-Induced Peripheral Neuropathy Model Rat

Model rats were prepared in the same manner as described in the section 2 of the Aforementioned Test by Single Intraperitoneal Administration of Oxaliplatin at a Dose of 6 mg/kg to 7-Weeks Old Sprague Dawley Male Rats.

(2) Administration of Test Drug

As single ART-123 administration group, ART-123 was intraperitoneally administered once to the rats, to which oxaliplatin had been administered, on the day of the oxaliplatin administration, and the medium was intraperitoneally administered once on each of the next day and the day after next day. As double ART-123 administration group, ART-123 was intraperitoneally administered once to the rats, to which oxaliplatin had been administered, on each of the day of the oxaliplatin administration and the next day, and the medium was intraperitoneally administered on the day after next day. As triple ART-123 administration group, ART-123 was intraperitoneally administered once to the rats, to which oxaliplatin had been administered, on each of the day of the oxaliplatin administration, the next day, and the day after next day. The administration dose of ART-123 was 1 mg/kg. As the negative control (medium group), the medium was intraperitoneally administred once a day for 3 days.

(3) Randall-Selitto Test

In the same manner as described in the section 2 of the aforementioned test, the right hind leg paw was gradually pressurized with a pressure pain analgesy meter, and the pressure observed when the animal showed an escape response was determined as the pressure pain escape threshold.

(4) Statistical Analysis

As for the action of ART-123, the pressure pain escape thresholds determined on the 14th and 21st days after the oxaliplatin administration were statistically analyzed. By using the medium group as a control, the parametric Williams test (ascending direction) was performed at a one-tailed significance level of 2.5% or less for the pressure pain escape thresholds observed for the single, double, and triple ART-123 administration groups (*: $p<0.05$, and **: $p<0.01$ in FIG. 2). Further, a paired t-test was performed at a two-tailed significance level of 5% for the pressure pain escape thresholds determined for the medium group one day before the oxaliplatin administration, and on the 14th or 21st day after the oxaliplatin administration (##: $p<0.01$ in FIG. 2).

<Results>

In the control group, the pressure pain escape threshold was significantly lowered on the 14th and 21st days after the oxaliplatin administration compared with that observed on the day before the oxaliplatin administration, and thus hyperalgesia was developed. When ART-123 was administered at a dose of 1 mg/kg once a day on each of the day of the oxaliplatin administration, the next day, and the day after next day, i.e., total three times, the hyperalgesia was significantly suppressed on the 14th day or the 21st day, which corresponds to the last day of one cycle of oxaliplatin treatment. On the other hand, when ART-123 was administered once on only the day of the oxaliplatin administration, the effect of maintaining suppression of hyperalgesia up to the 14th day or the 21st day, which corresponds to the last day of one cycle of oxaliplatin treatment, was weak or was not observed. The results are shown in FIG. 2.

That is, even with the intraperitoneal administration of ART-123 to the rat model at a dose of 1 mg/kg, which corresponds to about 3 to 6 times of the dose of 0.06 mg/kg of ART-123 for intravenous administration to a human, the effect of suppressing onset of a peripheral neuropathy could not be maintained over a period of 14 days or 21 days, which corresponds to one cycle of the oxaliplatin treatment. Namely, it was considered that, in humans, three times of intravenous administrations of ART-123 at a dose of 0.06 mg/kg in one cycle of the oxaliplatin treatment are necessary for suppressing onset of a peripheral neuropathy induced by oxaliplatin, whereas single intravenous administration of ART-123 at a dose of 0.06 mg/kg in one cycle of the oxaliplatin treatment cannot be expected to suppress onset of a peripheral neuropathy induced by oxaliplatin.

What is claimed is:

1. A method for mitigating conditions and/or suppressing onset of a peripheral neuropathy induced by an anti-malignant tumor agent in a human cancer patient receiving an anti-malignant tumor treatment with oxaliplatin,
   wherein the anti-malignant tumor treatment comprises repeating a single cycle of treatment, wherein the single cycle comprises:
   an intravenous administration period of oxaliplatin to the human cancer patient and,
   a subsequent oxaliplatin drug withdrawal period from the end of the intravenous administration period of oxaliplatin,
   wherein said method for mitigating conditions and/or suppressing onset comprises:
   intravenously administering 0.06 mg/kg of thrombomodulin to the human cancer patient,
   wherein the day of administration of thrombomodulin is the first day of each said single cycle,
   wherein the number of administrations of thrombomodulin during each said single cycle is one,
   wherein the day on which administration of oxaliplatin is started is defined as the first day of each said single cycle,
   wherein the administration of thrombomodulin ends before the start of the oxaliplatin administration, and
   wherein the thrombomodulin is a peptide containing the amino acid sequence of (i-1) or (i-2) mentioned below, and the peptide is a peptide having the thrombomodulin activities;
   (i-1) the amino acid sequence of the positions 19 to 516 in the amino acid sequence of SEQ ID NO: 1 or 3, or
   (i-2) the amino acid sequence of (i-1) mentioned above, further including substitution, deletion or addition of one or more amino acid residues and having a homology of 95% or higher with one of the amino acid sequences of (i-1).

2. The method according to claim 1, wherein the anti-malignant tumor treatment with oxaliplatin comprises repeating a single cycle comprising once per day of intravenous administration of oxaliplatin in an amount of 50 to 150 mg/m$^2$ of body surface area to the human cancer patient for 1 to 3 days, and then discontinuing oxaliplatin administration for at least 13 days during the oxaliplatin drug withdrawal period.

3. The method according to claim 1, wherein oxaliplatin is administered according to an anti-malignant tumor chemotherapy that uses oxaliplatin in combination with fluorouracil and levofolinate.

4. The method according to claim 1, comprising administering thrombomodulin to the cancer patient suffering from one or more kinds of cancers selected from the group consisting of large bowel cancer, pancreatic cancer, and gastric cancer.

5. The method according to claim 1, wherein the peripheral neuropathy is motor peripheral neuropathy or sensory peripheral neuropathy.

6. The method according to claim 1, wherein the thrombomodulin is soluble thrombomodulin.

7. The method according to claim 1, wherein the thrombomodulin is human thrombomodulin.

8. The method according to claim 1, wherein the thrombomodulin is a peptide obtainable from a transformed cell prepared by transfecting a host cell with a DNA coding for the amino acid sequence of (i-1) or (i-2) mentioned below (the peptide obtainable from a DNA coding for the amino acid sequence of (i-2) has the thrombomodulin activities);
- (i-1) the amino acid sequence of SEQ ID NO: 1 or 3, or
- (i-2) the amino acid sequence of (i-1) mentioned above, further including substitution, deletion or addition of one or more amino acid residues and having a homology of 95% or higher with one of the amino acid sequences of (i-1).

9. The method according to claim 1, wherein the thrombomodulin is Thrombomodulin alfa.

10. The method according to claim 2, wherein oxaliplatin is administered according to an anti-malignant tumor chemotherapy that uses oxaliplatin in combination with fluorouracil and levofolinate.

11. The method according to claim 2, comprising administering thrombomodulin to the cancer patient suffering from one or more kinds of cancers selected from the group consisting of large bowel cancer, pancreatic cancer, and gastric cancer.

12. The method according to claim 2, wherein the peripheral neuropathy is motor peripheral neuropathy or sensory peripheral neuropathy.

13. The method according to claim 2, wherein the thrombomodulin is soluble thrombomodulin.

14. The method according to claim 2, wherein the thrombomodulin is human thrombomodulin.

15. The method according to claim 2, wherein the thrombomodulin is a peptide obtainable from a transformed cell prepared by transfecting a host cell with a DNA coding for the amino acid sequence of (i-1) or (i-2) mentioned below (the peptide obtainable from a DNA coding for the amino acid sequence of (i-2) has the thrombomodulin activities);
- (i-1) the amino acid sequence of SEQ ID NO: 1 or 3, or
- (i-2) the amino acid sequence of (i-1) mentioned above, further including substitution, deletion or addition of one or more amino acid residues and having a homology of 95% or higher with one of the amino acid sequences of (i-1).

16. The method according to claim 2, wherein the thrombomodulin is Thrombomodulin alfa.

17. The method according to claim 2, wherein the anti-malignant tumor treatment with oxaliplatin comprises repeating a single cycle comprising once per day of intravenous administration of oxaliplatin in an amount of 50 to 150 mg/m$^2$ of body surface area to the human cancer patient for 1 day, and then discontinuing oxaliplatin administration for at least 13 days during the oxaliplatin drug withdrawal period.

18. The method according to claim 17, wherein the thrombomodulin is a peptide obtainable from a transformed cell prepared by transfecting a host cell with a DNA coding for the amino acid sequence of (i-1) or (i-2) mentioned below (the peptide obtainable from a DNA coding for the amino acid sequence of (i-2) has the thrombomodulin activities);
- (i-1) the amino acid sequence of SEQ ID NO: 1 or 3, or
- (i-2) the amino acid sequence of (i-1) mentioned above, further including substitution, deletion or addition of one or more amino acid residues and having a homology of 95% or higher with one of the amino acid sequences of (i-1).

19. The method according to claim 17, wherein the thrombomodulin is Thrombomodulin alfa.

* * * * *